US011326870B2

(12) United States Patent
Izatt et al.

(10) Patent No.: US 11,326,870 B2
(45) Date of Patent: May 10, 2022

(54) SYSTEMS AND METHODS FOR ENHANCED RESOLUTION IMAGING BASED ON MULTIPLE CROSS-SECTIONAL IMAGES ACQUIRED AT DIFFERENT ANGLES

(71) Applicant: Duke University, Durham, NC (US)

(72) Inventors: Joseph Izatt, Durham, NC (US); Ruobing Qian, Durham, NC (US); Sina Farsiu, Durham, NC (US); Kevin Zhou, Durham, NC (US)

(73) Assignee: Duke University, Durham, NC (US)

( * ) Notice: Subject to any disclaimer, the term of this patent is extended or adjusted under 35 U.S.C. 154(b) by 56 days.

(21) Appl. No.: 16/955,754

(22) PCT Filed: Jan. 29, 2019

(86) PCT No.: PCT/US2019/015540
§ 371 (c)(1),
(2) Date: Jun. 18, 2020

(87) PCT Pub. No.: WO2019/148158
PCT Pub. Date: Aug. 1, 2019

(65) Prior Publication Data
US 2020/0340798 A1    Oct. 29, 2020

Related U.S. Application Data

(60) Provisional application No. 62/623,044, filed on Jan. 29, 2018.

(51) Int. Cl.
*G01B 9/02091*  (2022.01)
*G01B 9/02015*  (2022.01)
(Continued)

(52) U.S. Cl.
CPC ....... *G01B 9/02091* (2013.01); *G01B 9/0203* (2013.01); *G01N 21/4795* (2013.01);
(Continued)

(58) Field of Classification Search
CPC ................ G01B 9/02091; G01B 9/0203; G06T 3/0068; G06T 7/37; G06T 7/30;
(Continued)

(56) References Cited

U.S. PATENT DOCUMENTS

| 2011/0032553 A1 | 2/2011 | Izatt et al. | |
| 2014/0241605 A1* | 8/2014 | Izatt | A61B 3/102 382/131 |

(Continued)

OTHER PUBLICATIONS

Abadi, M. et al., TensorFlow: Large-Scale Machine Learning on Heterogeneous Distributed Systems, Nov. 9, 2015, 1-19, TensorFlow, Mountain View, California. (Nineteen (19) pages).
(Continued)

*Primary Examiner* — Chan S Park
*Assistant Examiner* — Daniel C Chang
(74) *Attorney, Agent, or Firm* — Olive Law Group, PLLC

(57) ABSTRACT

Systems and methods for imaging based on multiple cross-sectional images acquired at different angles are disclosed. According to an aspect, multiple cross-sectional images of an object are acquired at different angles. The method also includes registering the acquired cross-sectional images. Further, the method includes reconstructing an enhanced resolution image of the object based on the registered images. As a result of registering the images, a distortion map is generated that is coregistered with the high-resolution image. The method also includes displaying an image of the object based on the enhanced resolution image and the distortion map.

17 Claims, 13 Drawing Sheets

(51) Int. Cl.
G01N 21/47 (2006.01)
G06T 3/00 (2006.01)
G06T 7/37 (2017.01)
G06T 7/30 (2017.01)
A61B 5/00 (2006.01)

(52) U.S. Cl.
CPC .............. *G06T 3/0068* (2013.01); *G06T 7/30* (2017.01); *G06T 7/37* (2017.01); *A61B 5/0066* (2013.01)

(58) Field of Classification Search
CPC ....... G06T 15/04; G06T 15/08; A61B 5/0066; G01N 21/4795
See application file for complete search history.

(56) References Cited

U.S. PATENT DOCUMENTS

| | | | |
|---|---|---|---|
| 2015/0092197 A1 | 4/2015 | Massow et al. | |
| 2015/0150447 A1 | 6/2015 | Huang et al. | |
| 2015/0243045 A1* | 8/2015 | Ra | A61B 6/032 382/131 |
| 2016/0038021 A1 | 2/2016 | Bagherinia et al. | |
| 2021/0210169 A1* | 7/2021 | Meyer | G06K 9/00147 |

OTHER PUBLICATIONS

Binding, J. et al., Brain Refractive Index Measured in Vivo with High-NA Defocus-corrected Full-field OCT and Consequences for Two-photon Microscopy, Optics Express, Mar. 14, 2011, 4833-4847, 19(6), OSA Publishing, Washington, D.C. (Fifteen (15) pages).
Blatter, C. et al., Extended Focus High-speed Swept Source OCT with Self-reconstructive Illumination, Optics Express, Jun. 20, 2011, 12141-12155, 19(13), OSA Publishing, Washington, D.C. (Fifteen (15) pages).
Bo, E. et al., Depth-of-focus Extension in Optical Coherence Tomography Via Multiple Aperture Synthesis, Optica, Jul. 2017, 701-706, 4(7), Optical Society of America, Rochester, New York. (Six (6) pages).
Carrasco-Zevallos, O. et al., Pupil Tracking Optical Coherence Tomography for Precise Control of Pupil Entry Position, Biomedical Optics Express, Sep. 1, 2015, 3405-3419, 6(9), OSA Publishing, Washington, D.C. (Fifteen (15) pages).
Chowdhury, S. et al., Refractive Index Tomography with Structured Illumination, Optica, May 10, 2017, 537-545, 4 (5), Optical Society of America, Rochester, New York. (Nine (9) pages).
Desjardins, A.E. et al., Speckle Reduction in OCT Using Massively-parallel Detection and Frequency-domain Ranging, Optics Express, May 29, 2006, 4736-4745, 14(11), OSA Publishing, Washington, D.C. (Ten (10) pages).
Dormand, J.R. et al., A Family of Embedded Runge-Kutta Formulae, Journal of Computational and Applied Mathematics, 1980, 19-26, 6(1), Elsevier, Amsterdam. (Eight (8) pages).
Flolka, R. et al., Simplified Approach to Diffraction Tomography in Optical Microscopy, Optics Express, 12407-12417, 17(15), OSA Publishing, Washington, D.C. (Eleven (11) pages).
Fuchs, S. et al., Optical Coherence Tomography with Nanoscale Axial Resolution Using a Laser-driven High-harmonic Source, Optica, Aug. 2017, 903-906, 4(8), Optical Society of America, Rochester, New York. (Four (4) pages).
Guizar-Sicairos, M. et al., Efficient Subpixel Image Registration Algorithms, Optics Letters, Jan. 15, 2008, 156-158, 33(2), OSA Publishing, Washington, D.C. (Three (3) pages).
Hitzenberger, C.K., Optical Measurement of the Axial Eye Length by Laser Doppler Interferometry, investigative Opthalmology & Visual Science, Mar. 1991,616-624, 32(3), ARVO Journals, Rockville, Maryland. (Nine (9) pages).
Horstmeyer, R. et al., Diffraction Tomography with Fourier Ptychography, Optica, Jul. 27, 2016, 827-835, 3(8), Optical Society of America, Rochester, New York. (Nine (9) pages).
Huang, D. et al., Optical Coherence Tomography, Science, Nov. 22, 1991, 1178-1181, 254(5035), American Association for the Advancement of Science, Washington, D.C. (Twelve (12) pages).
Iftimia, N. et al., Speckle Reduction in Optical Coherence Tomography by "path length encoded" Angular Compounding, Journal of Biomedical Optics, Apr. 2003, 260-263, 8(2), SPIE, Bellingham, Washington. (Four (4) pages).
Kaganovsky, Y. et al., Compressed Sampling Strategies for Tomography, Journal of the Optical Society of America, Jul. 2014, 1369-1394, 31(7), OSA Publishing, Washington, D.C. (Twenty-six (26) pages).
Kim, Y.L. et al., Variation of Corneal Refractive Index with Hydration, Physics in Medicine and Biology, Jan. 14, 2004, 859-868, 49, Institute on Physics Publishing Bristol, United Kingdom. (Eleven (11) pages).
Kingma, D.P. et al., Adam: A Method for Stochastic Optimization, ICLR 2015, 1-15, International Conference on Representation Learning, La Jolla, California. (Fifteen (15) pages).
Kitazawa, T. et al., Refractive Index Tomography Based on Optical Coherence Tomography and Tomographic Reconstruction Algorithm, Japanese Journal of Applied Physics, Jul. 10, 2018, 09NB03, 57, The Japan Society of Applied Physics, Tokyo. (Eight (8) pages).
Knüttel, A. et al., Spatially Confined and Temporally Resolved Refractive Index and Scattering Evaluation in Human Skin Performed with Optical Coherence Tomography, Journal of Biomedical Optics, Jan. 2000, 83-92, 5(1), SPIE, Bellingham, Washington. (Ten (10) pages).
Lee, K. et al., Bessei Beam Spectral-domain High-resolution Optical Coherence Tomography with Micro-optic Axicon Providing Extended Focusing Range, Optics Letters, Aug. 1, 2008, 1696-1698, 33(15), Optical Society of America, Rochester, New York. (Three (3) pages).
Lim, J. et al., Comparative Study of Iterative Reconstruction Algorithms for Missing Cone Problems in Optical Diffraction Tomography, Optics Express, Jun. 29, 2015, 16933-16948, 23(13), OSA Publishing, Washington, D.C. (Sixteen (16) pages).
Liu, L. et al., Imaging the Subcellular Structure of Human Coronary Atherosclerosis Using Micro-optical Coherence Tomography, Nature Medicine, Aug. 2011, 1010-1014, 17(8), Springer Nature, New York. (six (6) pages).
Lorenser, D. et al., Ultrathin Fiber Probes with Extended Depth of Focus for Optical Coherence Tomography, Optics Letters, May 15, 2012, 1616-1618, 37(10), OSA Publishing, Washington, D.C. (Three (3) pages).
Mo, J. et al., Focus-extension by Depth-encoded Synthetic Aperture in Optical Coherence Tomography, Optics Express, Apr. 22, 2013, 10048-10061, 21(8), OSA Publishing, Washington, D.C. (Fourteen (14) pages).
Nadaraya, E.A. et al., On Estimating Regression, Teor. Veroyatnost. i Primenen., 1964, 157-159, 9(1), Math-Net. RU. (Four (4) pages).
Ortiz, S. et al., Optical Distortion Correction in Optical Coherence Tomography for Quantitative Ocular Anterior Segment by Three-dimensional Imaging, Optics Express, Feb. 1, 2010, 2782-2796, 18(3), OSA Publishing, Washington, D.C. (Fifteen (15) pages).
Podoleanu, A. et al., Correction of Distortions in Optical Coherence Tomography Imaging of the Eye, Physics in Medicine & Biology, Mar. 18, 2004, 1277-1294, 49, institute of Physics Publishing, Bristol, United Kingdom. (Nineteen (19) pages).
Povasay, B. et al., Submicrometer Axial Resolution Optical Coherence Tomography, Optics Letters, Oct. 15, 2002, 1800-1802, 27(20), OSA Publishing, Washington, D.C. (Three (3) pages).
Ralsion, T.S. et al., Interferometric Synthetic Aperture Microscopy, Nature Physics, Feb. 2007, 129-134, 3, Nature Publishing Group, London. (Six (6) pages).
Rudin, L.I. et al., Nonlinear Total Variation Based Notice Removal Algorithms, Physica D, 1992, 259-268, 60, Elsevier, Amsterdam. (Ten (10) pages).
Shepp, L.A. et al., The Fourier Reconstruction of a head Section, IEE Transactions on Nuclear Science, Jun. 1974, 21-43, NS-21, IEEE, New York City. (Twenty three (23) pages).

(56) References Cited

OTHER PUBLICATIONS

Sung, Y. et al., Optical Diffraction Tomography for High Resolution Live Cell Imaging, Optics Express, 266-277, 17(1), OSA Publishing, Washington, D.C. (Twelve (12) pages).

Tam, K.C. et al., Tomographical Imaging with Limited-angle Input, Journal of the Optical Society of America, May 1981, 582-592, 71(5), OSA Publishing, Washington, D.C. (Eleven (11) pages).

Tearney, G.J. et al., Determination of the Refractive Index of Highly Scattering Human Tissue by Optical Coherence Tomography, Optics Letters, Nov. 1, 1995, 2258-2260, 20(21), OSA Publishing, Washington, D.C. (Three (3) pages).

Vermeer, K.A. et al., Depth-resolved Model-based Reconstruction of Attenuation Coefficients in optical Coherence Tomography, Biomedical Optics Express, Jan. 1, 2014, 322-337, 5(1), OSA Publishing, Washington, D.C. (Sixteen (16) pages).

Wang, H. et al., Speckle Reduction in Optical Coherence Tomography Using Angular Compounding by B-scan Doppler-shift Encoding, Journal of Biomedical Optics, 2009, 030512, 14(3), SPIE, Bellingham, Washington. (Eight (8) pages).

Wang, Y. et al., High-resolution Computed Tomography of Refractive Index Distribution by Transillumination Low-coherence Interferometry, Optics Letters, Jan. 1, 2010, 91-93, 35(1), OSA Publishing, Washington, D.C. (Three (3) pages).

Westphal, V. et al., Correction of Geometric and Refractive Image Distortions in Optical Coherence Tomography Applying Fermat's Principle, Optics Express, May 6, 2002, 397-404, 10(9), OSA Publishing, Washington, D.C. (Eight (8) pages).

Wu, C. et al., Comparison and Combination of Rotational Imaging Optical Coherence Tomography and Selective Plan Illumination Microscopy for Embryonic Study, Biomedical Optics Express, Oct. 1, 2017, 4629-4639, 8(10), Optical Society, Washington, D.C. (Eleven (11) pages).

Yao, J. et al., Angular Scan Optical Coherence Tomography Imaging and Metrology of Spherical Gradient Refractive Index Preforms, Optics Express, Mar. 5, 2015, 6428-6443, 23(5), OSA Publishing, Washington, D.C. (Sixteen (16) pages).

Zvyagin, A.V. et al., Refractive Index Tomography of Turbid Media by Bifocal Optical Coherence Refractometry, Optics Express, Dec. 15, 2003, 3503-3517, 11(25), OSA Publishing, Washington, D.C. (Fifteen (15) pages).

Zysk, A.M. et al., Projected Index Computed Tomography, Optics Letters, May 1, 2003, 701-703, 28(9), OSA Publishing, Washington, D.C. (Three (3) pages).

International Preliminary Report in related PCT case PCT/US2019/015540 dated Aug. 4, 2020. (Seven (7) pages).

PCT Search Report and Written Opinion for PCT International Patent Application No. PCT/US19/15540, dated May 14, 2019.

PCT Written Opinion of the International Searching Authority for PCT International Patent Application No. PCT/US19/15540, dated May 14, 2019.

\* cited by examiner

SYSTEMS AND METHODS FOR ENHANCED RESOLUTION IMAGING BASED ON MULTIPLE CROSS-SECTIONAL IMAGES ACQUIRED AT DIFFERENT ANGLES

CROSS REFERENCE TO RELATED APPLICATION

This is a 371 national stage patent application, which claims priority to PCT International Patent Application No. PCT/US2019/015540, filed Jan. 29, 2019, and titled SYSTEMS AND METHODS FOR ENHANCED RESOLUTION IMAGING BASED ON MULTIPLE CROSS-SECTIONAL IMAGES ACQUIRED AT DIFFERENT ANGLES, which claims priority to U.S. Patent Application No. 62/623,044, filed Jan. 29, 2018, and titled SYSTEMS AND METHODS FOR OPTICAL COHERENCE REFRACTION TOMOGRAPHY; the disclosures of which are incorporated herein by reference in their entireties.

FEDERALLY SPONSORED RESEARCH OR DEVELOPMENT

This invention was made with government support under grant number DGF-1106401 awarded by the National Science Foundation (NSF). The government has certain rights to this invention.

TECHNICAL FIELD

The presently disclosed subject matter relates generally to imaging. Particularly, the presently disclosed subject matter relates to systems and methods for imaging based on multiple cross-sectional images acquired at different angles to enhance resolution.

BACKGROUND

Optical coherence tomography (OCT) is a cross-sectional, micron-scale imaging modality based on coherence gating for depth resolution that has become the clinical standard of care for pathological diagnosis and treatment monitoring in several medical specialties. The axial resolution is determined by the coherence length of the light source and can be sub-micrometer. However, in a tradeoff necessitated by diffraction, conventional implementations of OCT typically accept an inferior lateral resolution, on the order of 10 µm or greater, in order to obtain a long depth of focus for bulk tissue imaging. Previous studies have addressed this tradeoff using techniques such as digital refocusing and beam-shaping, but in all cases the lateral resolution was still limited by diffraction.

Another limitation of conventional OCT is that images are distorted due to spatially inhomogeneous refractive index (RI) distributions in tissue. Previous attempts to correct such RI-induced distortions required a priori information on both the sample geometry and RI values, which severely limits the generalizability of such techniques.

In view of the foregoing, there is a need for improved OCT systems and techniques that limit image distortions and provides improved image resolution and contrast.

BRIEF DESCRIPTION OF THE DRAWINGS

Figure 1:
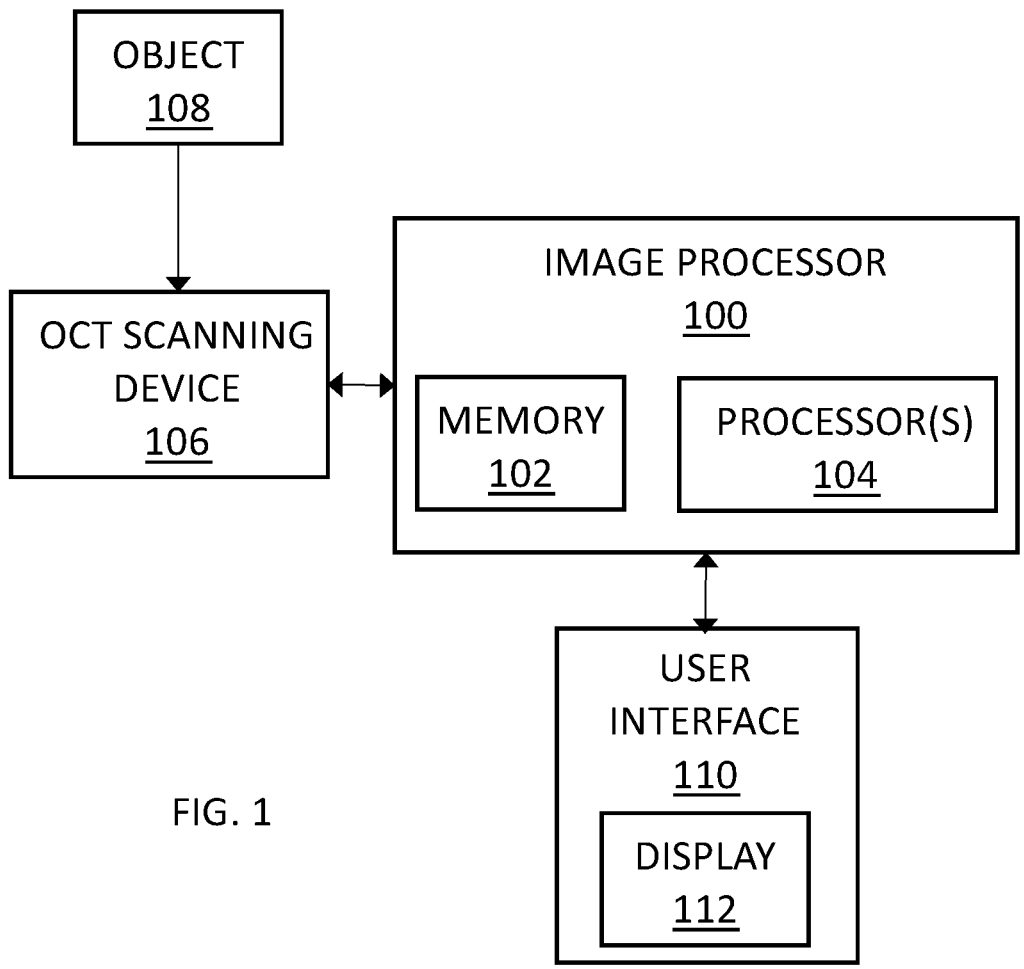
Figure 2A:
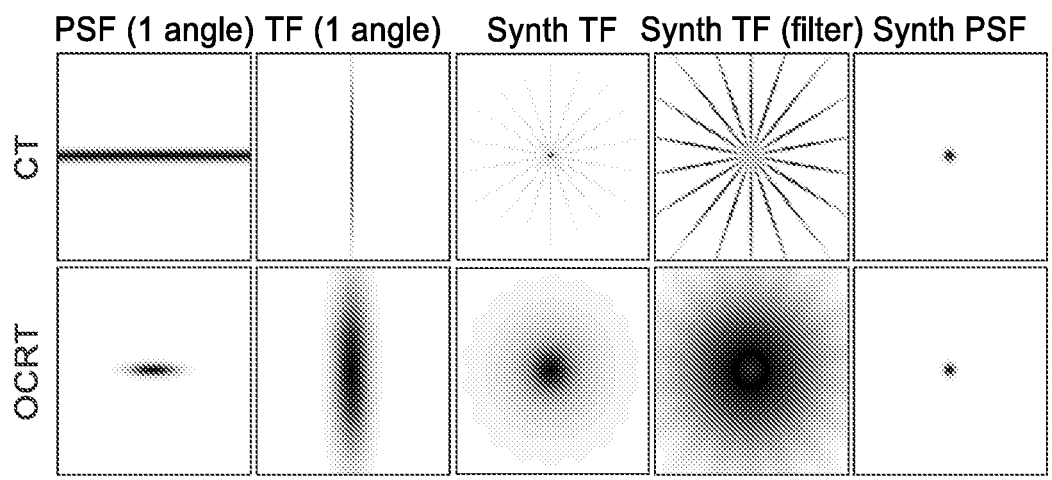
Figure 2B:
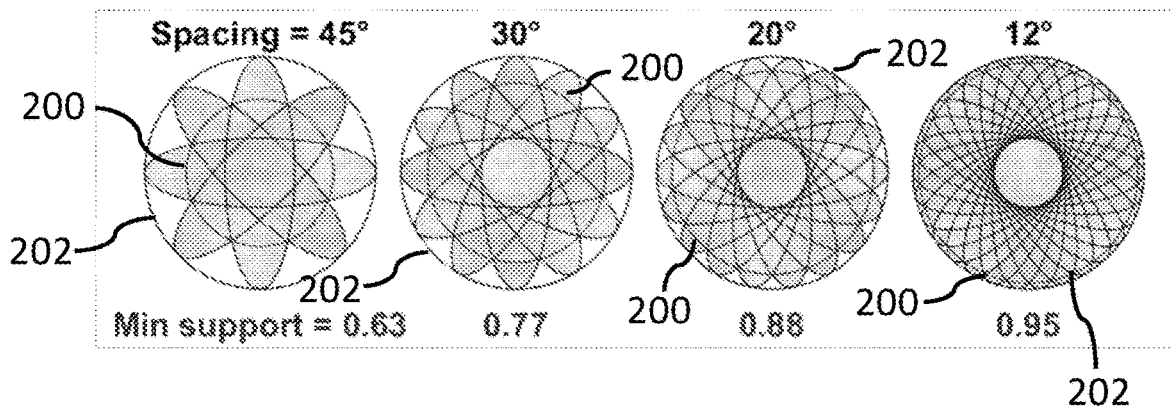
Figure 2C:
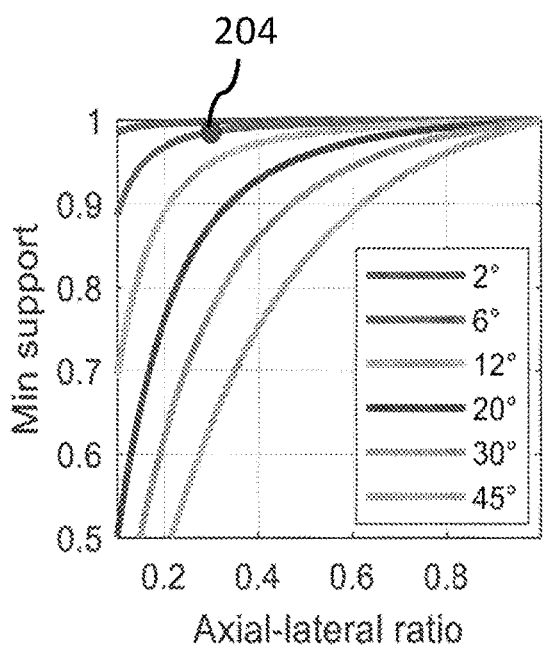
Figure 2D:
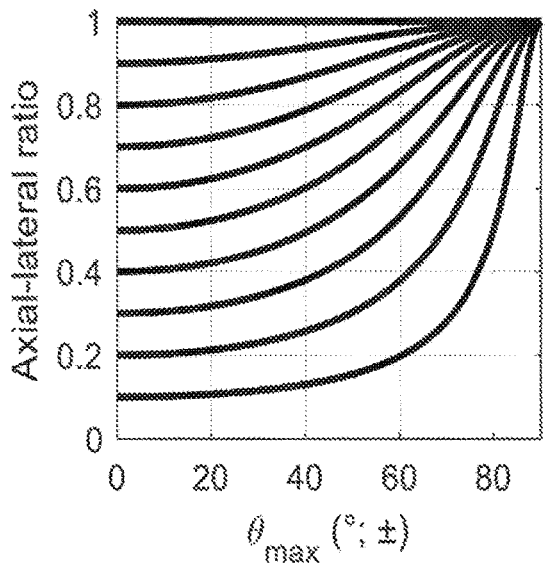
Figure 3:
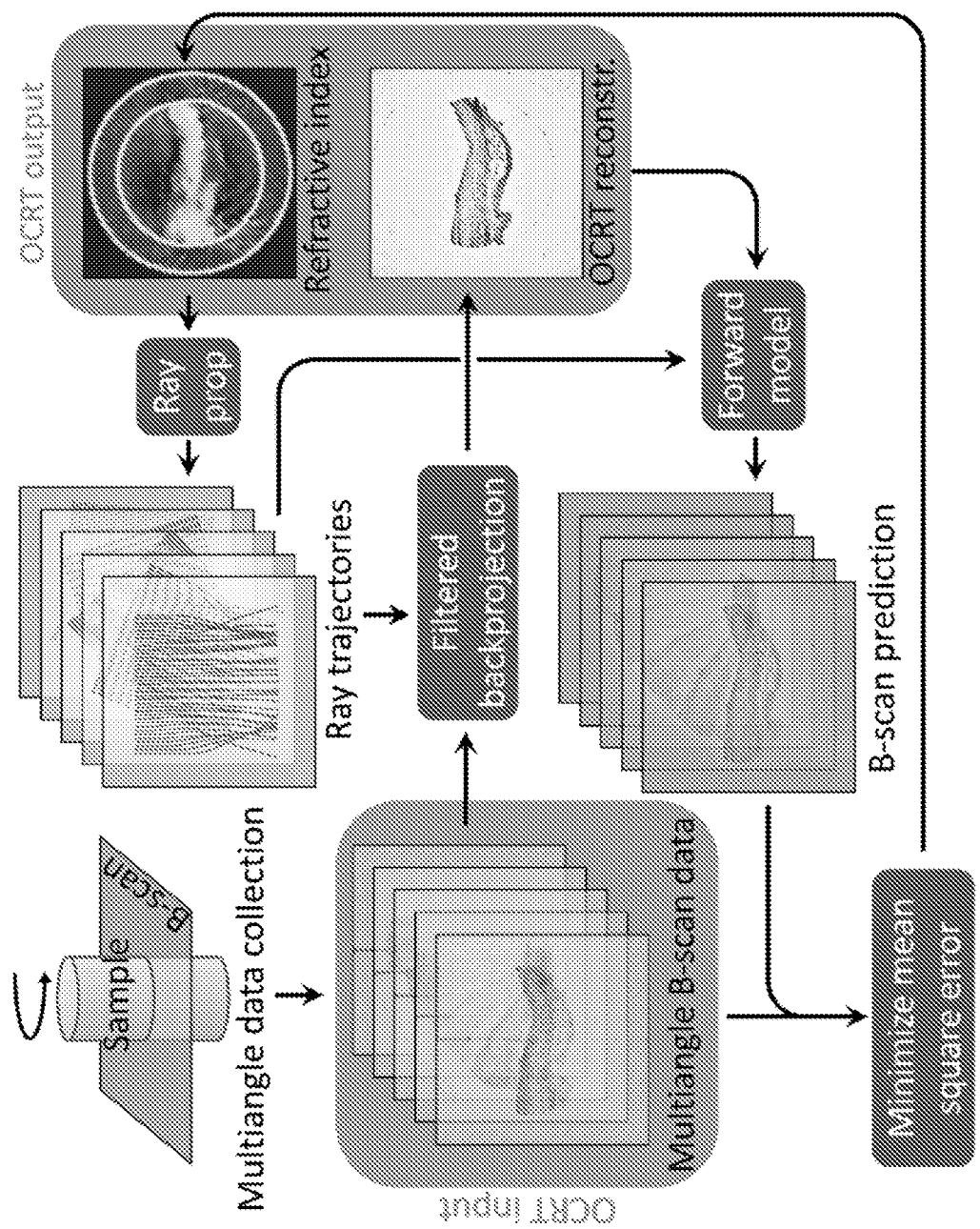
Figure 4:
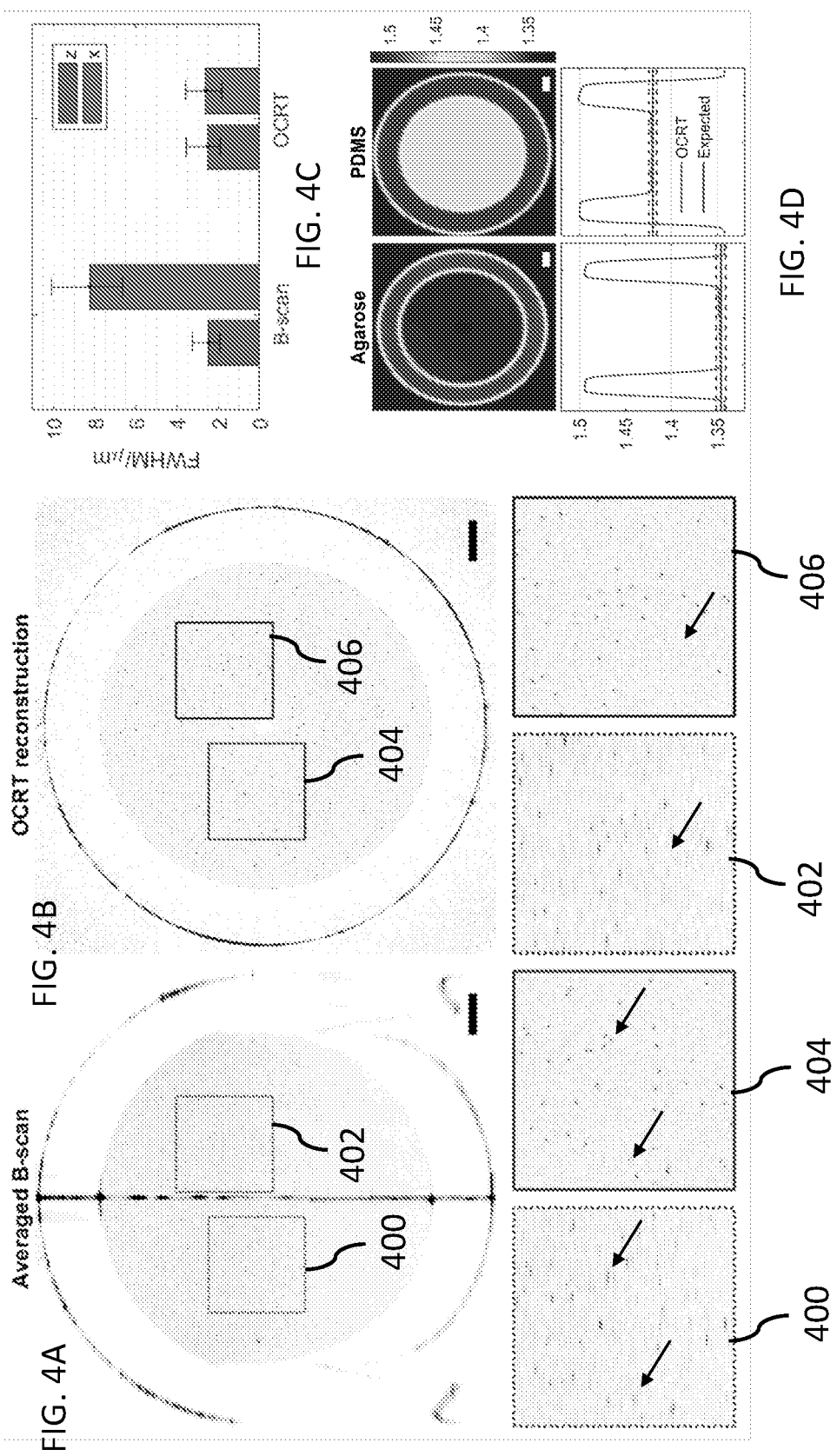
Figure 5:
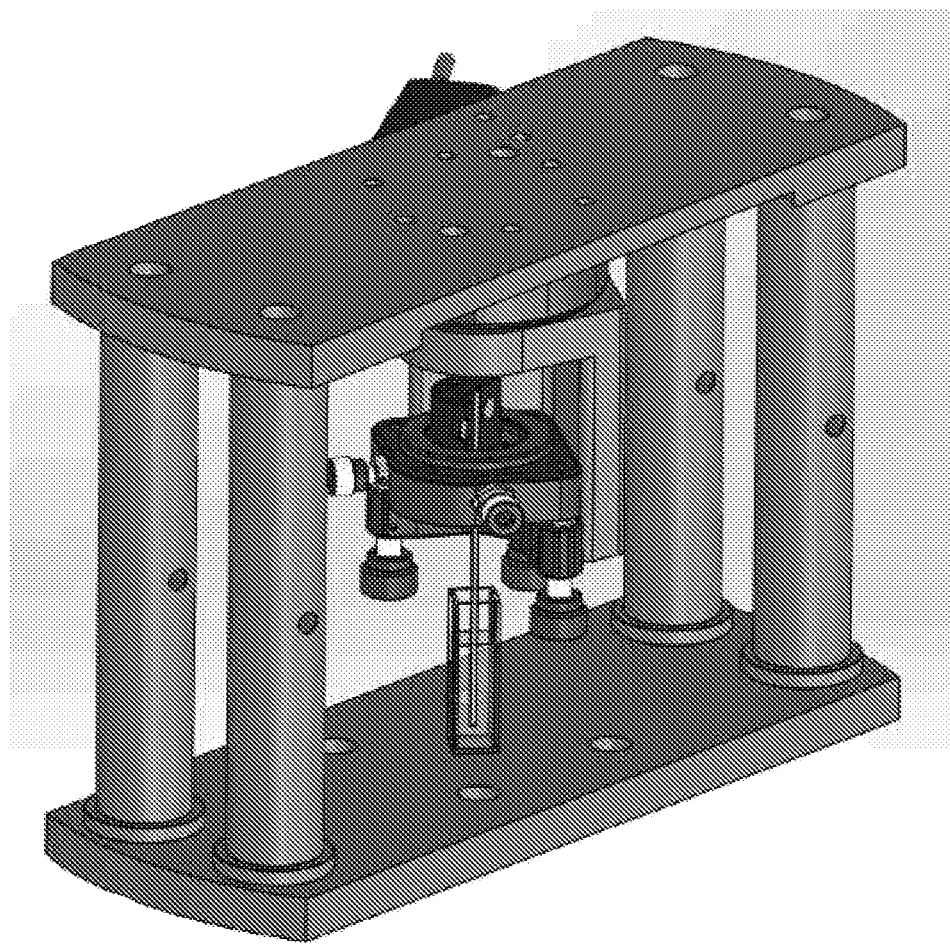
Figure 6:
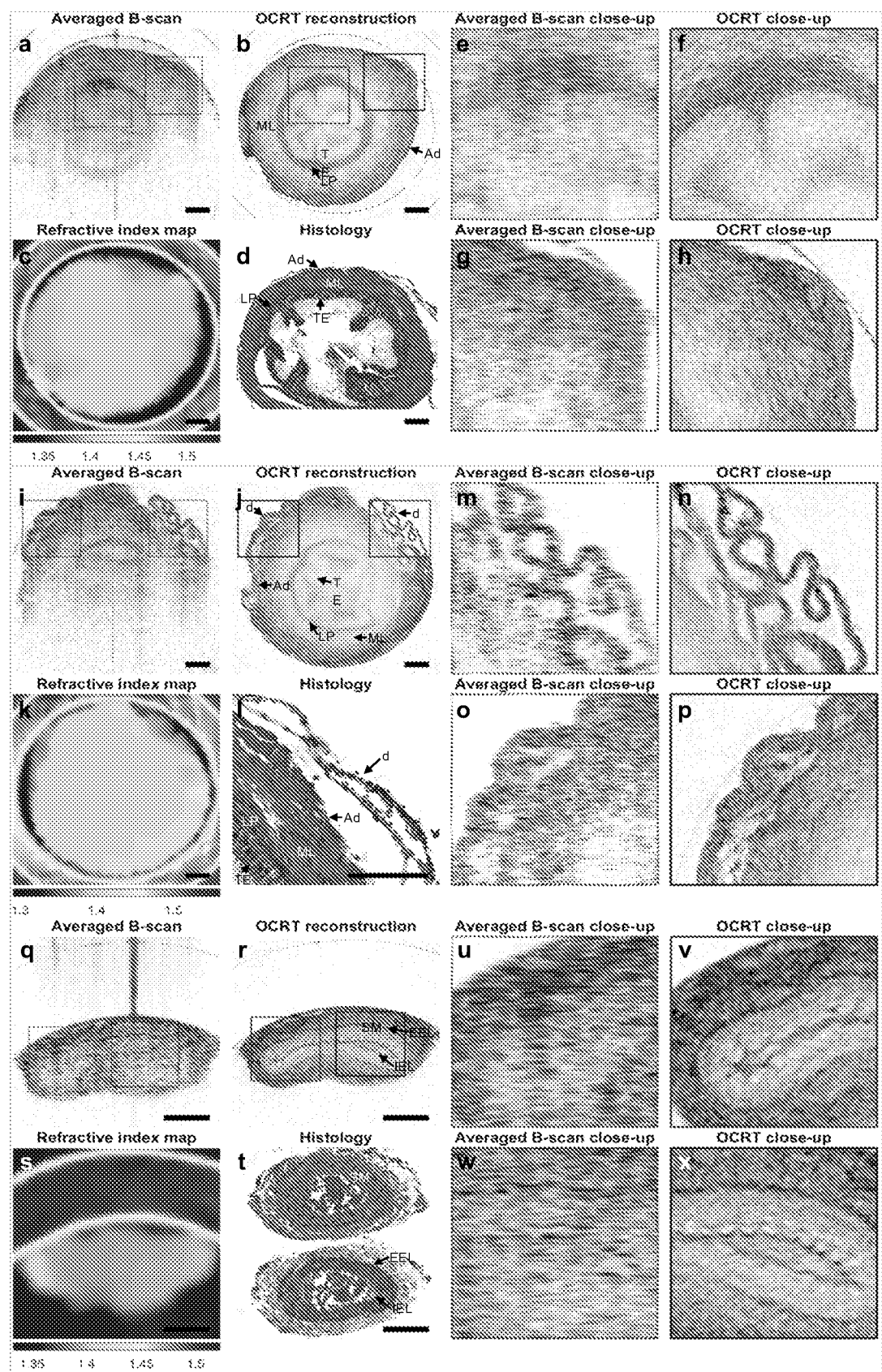
Figure 7A:
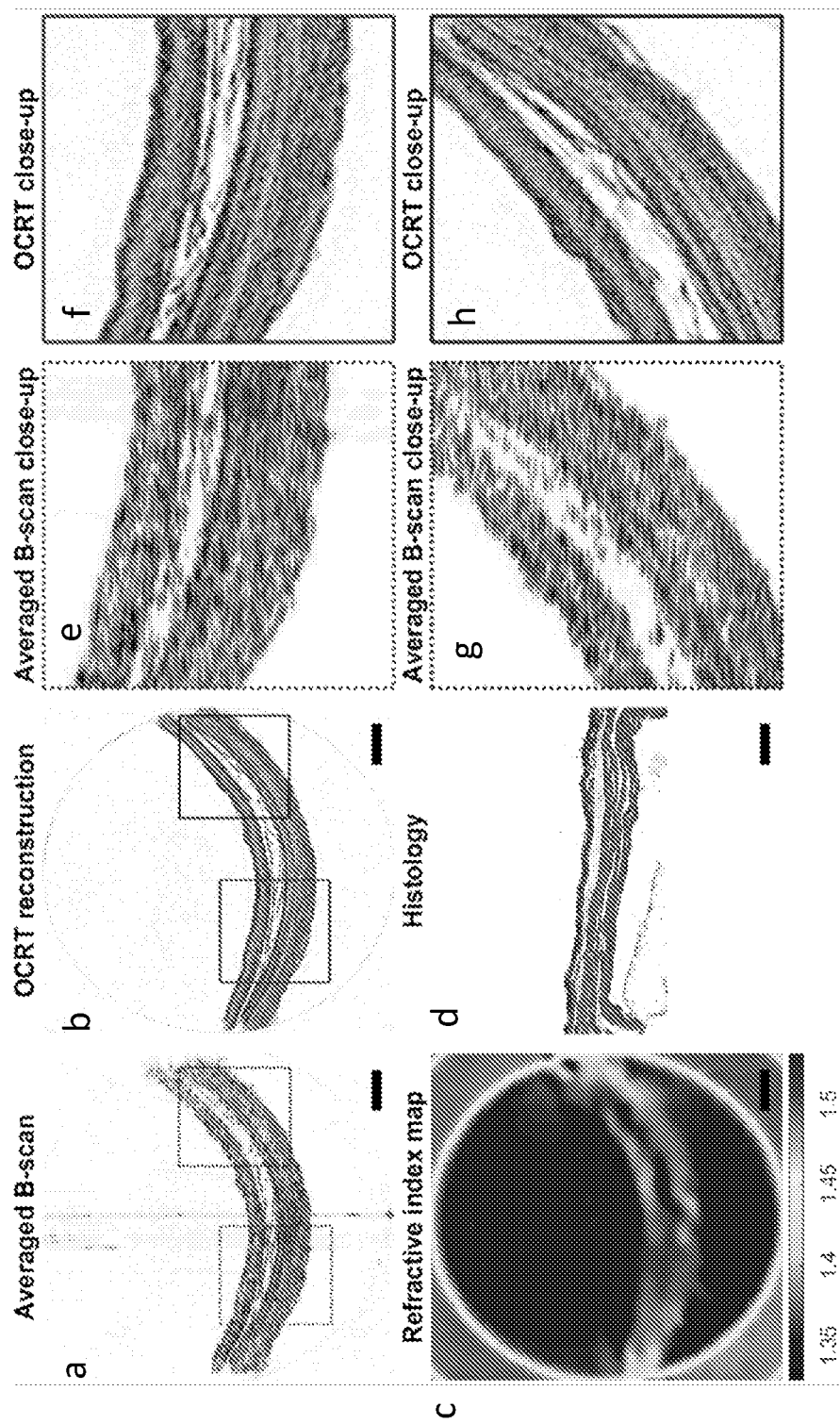
Figure 7B:
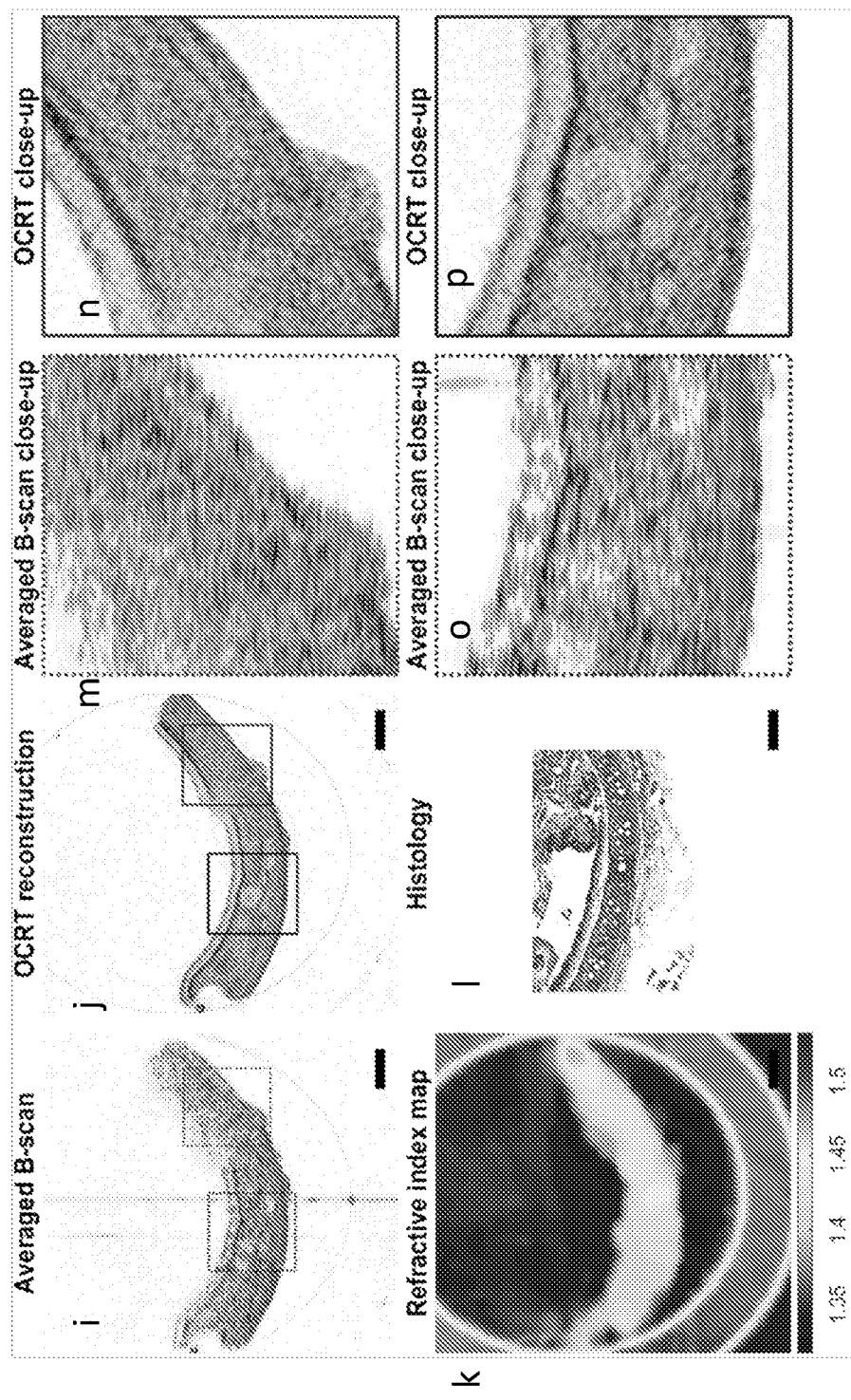
Figure 8:
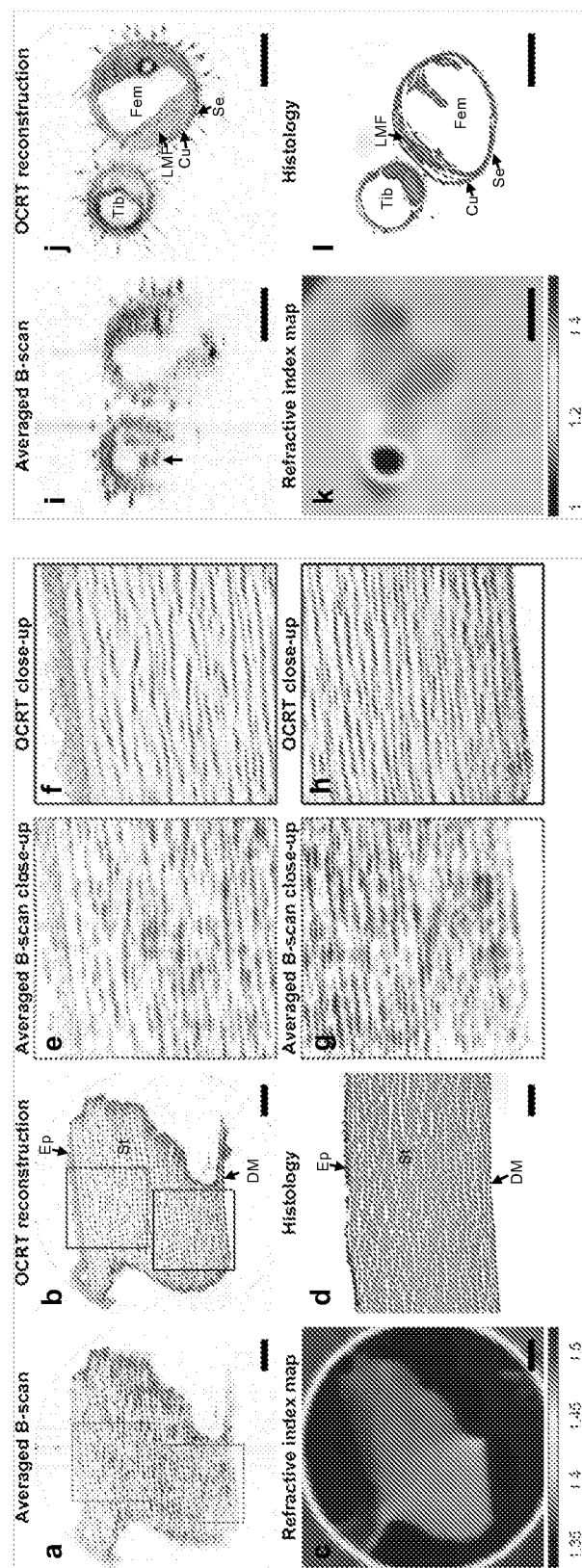
Figure 9:
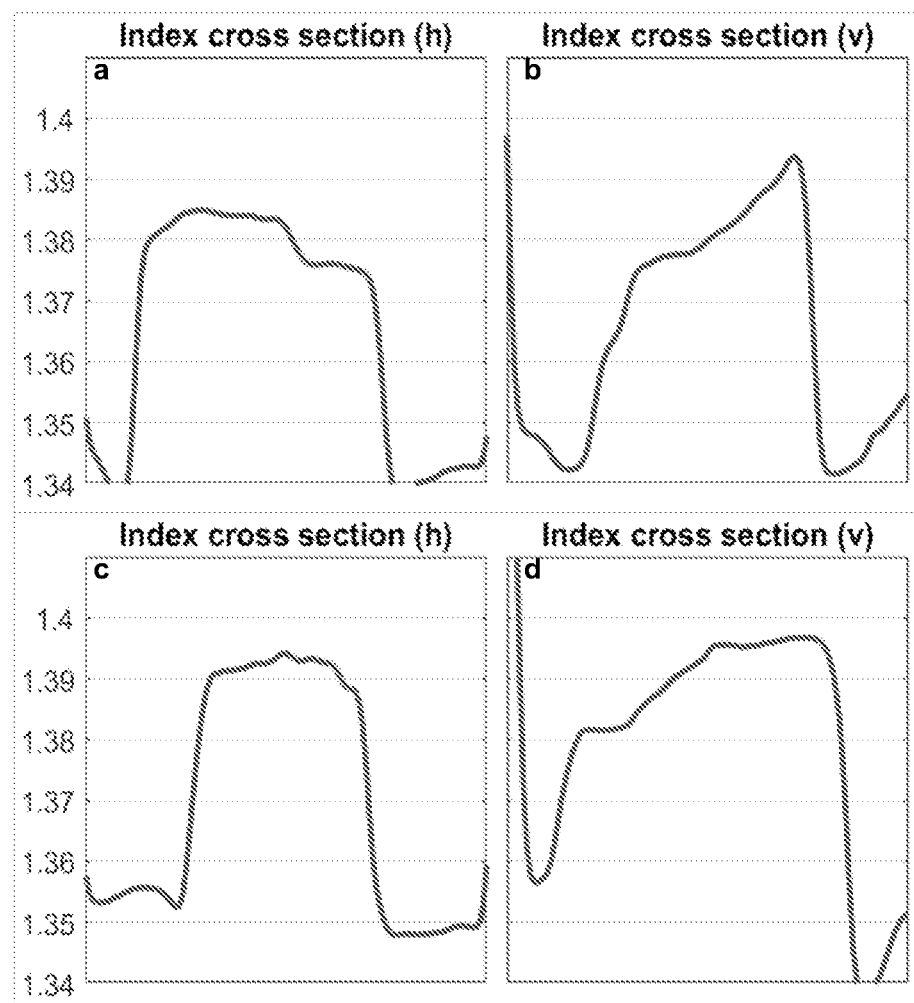
Figure 10:
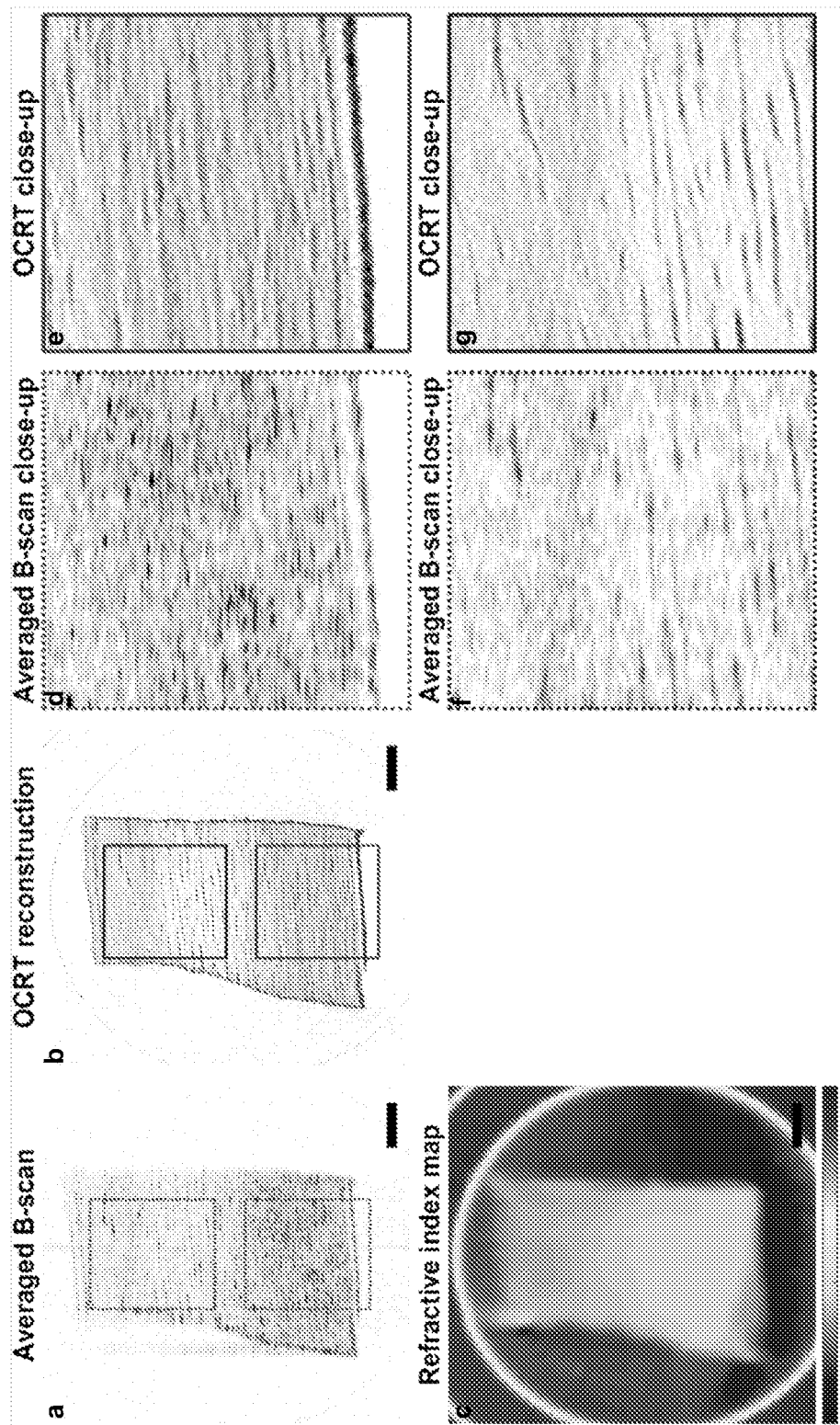
Figure 11:
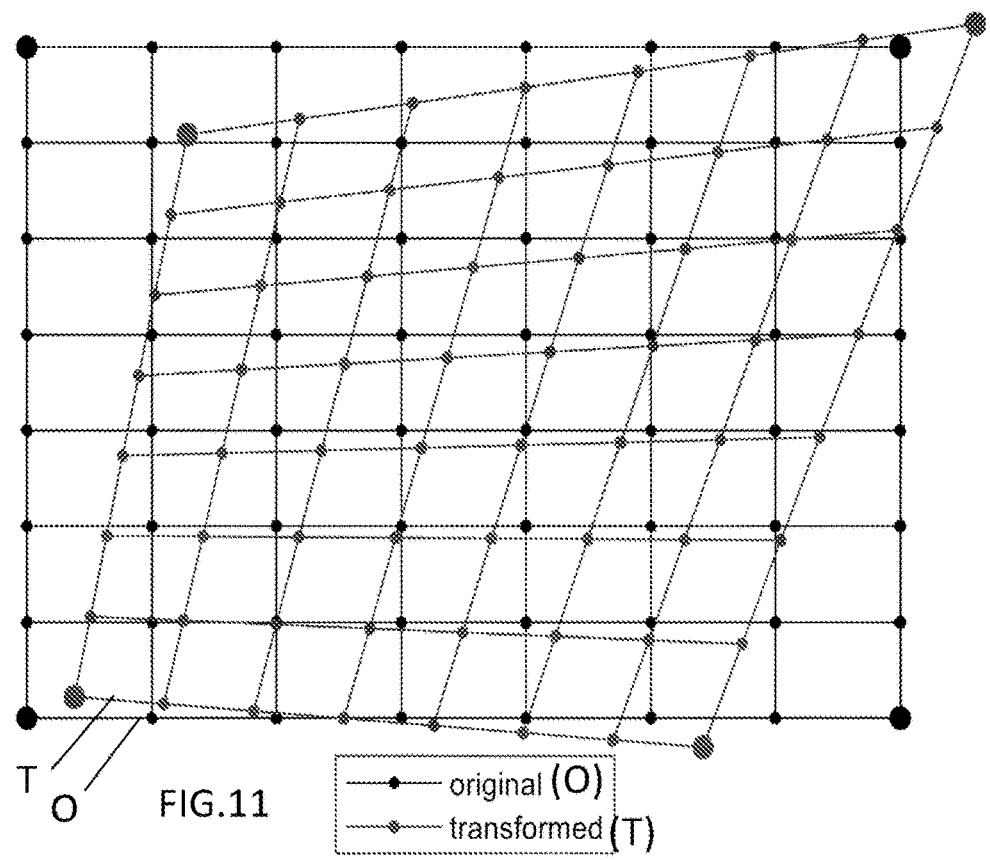
Figure 12:
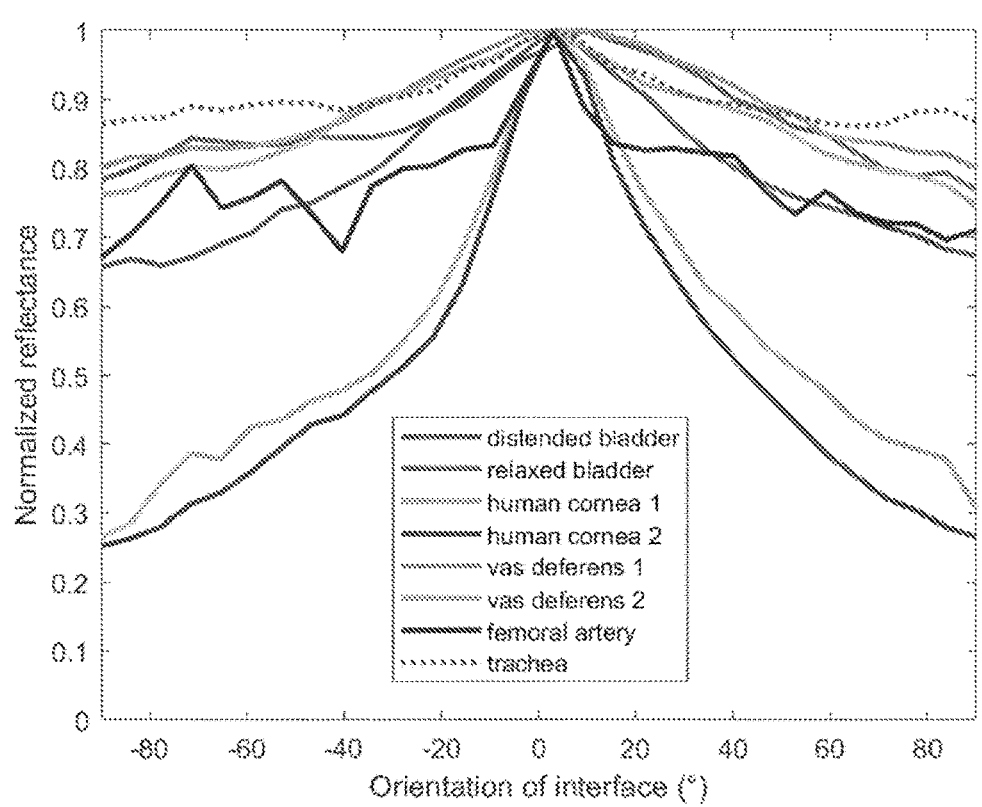
Figure 13:
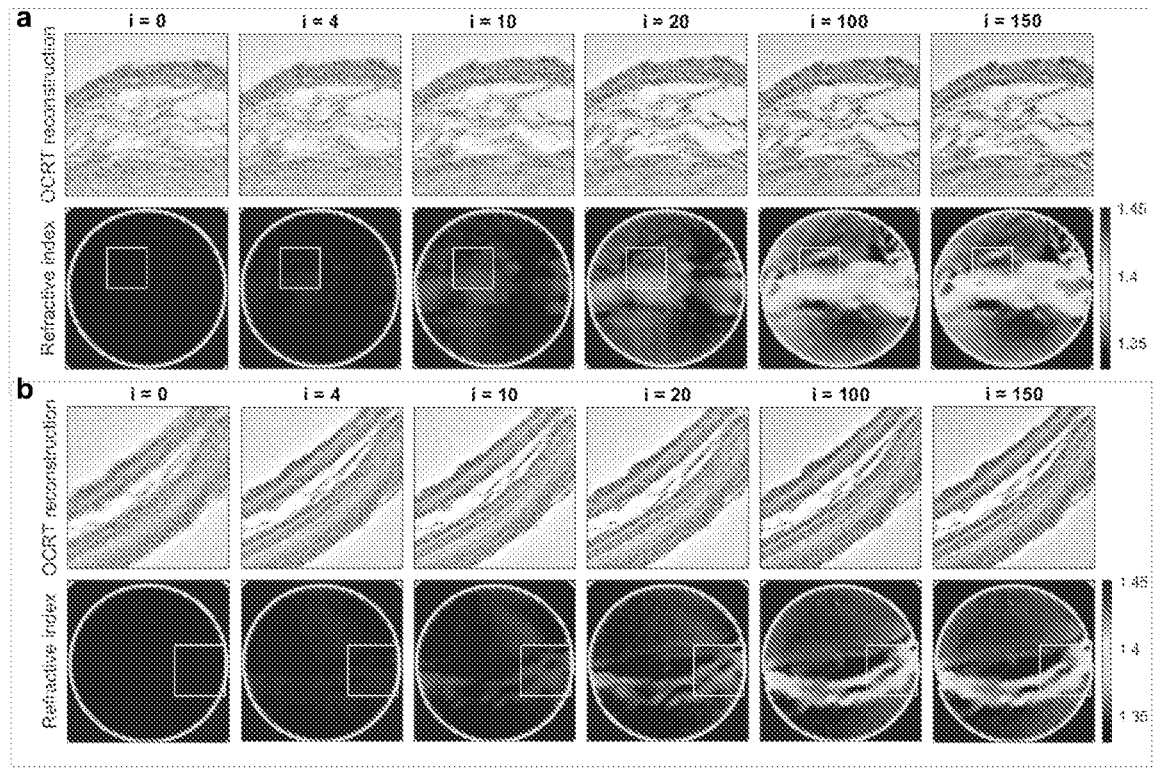
Figure 14:
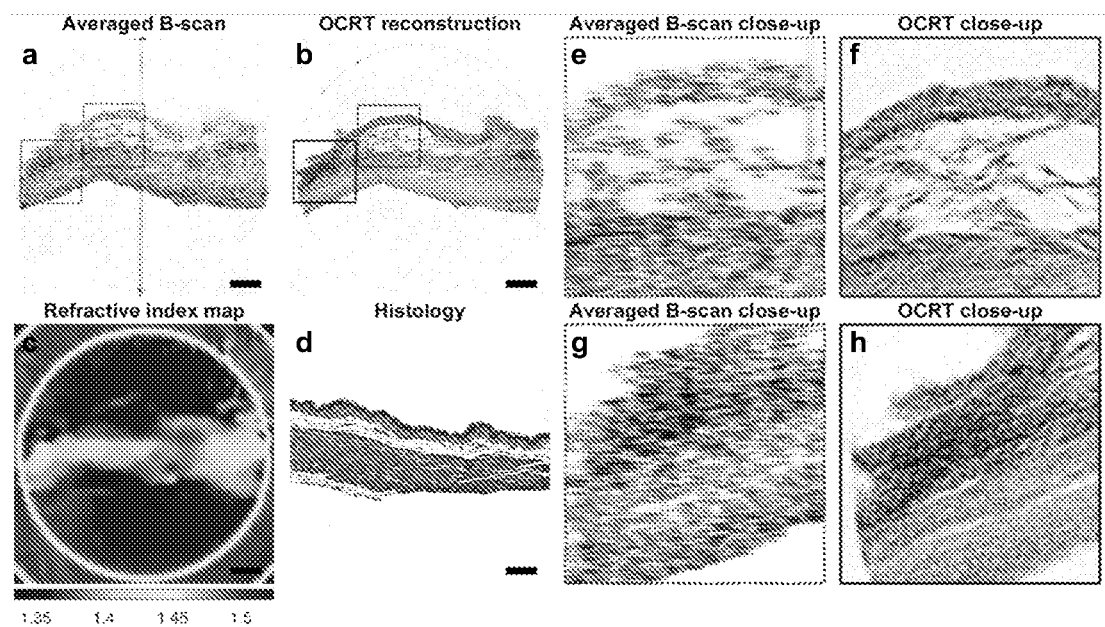

Having thus described the presently disclosed subject matter in general terms, reference will now be made to the accompanying Drawings, which are not necessarily drawn to scale, and wherein:

FIG. 1 is a block diagram of an example system for implementing optical coherence refraction tomography in accordance with embodiments of the present disclosure;

FIG. 2A are images showing CT and OCRT (top row of images and bottom row of images, respectively) as both having anisotropic lateral and vertical point-spread functions (PSFs) and transfer functions (TFs);

FIGS. 2B and 2C are diagrams and a graph, respectively, that show that angular spacings are dependent upon the axial-to-lateral resolution ratio and the amount of tolerance on the gaps in the Fourier space at intermediate angles;

FIG. 2D is a graph showing the axial-lateral ratio versus illumination angle;

FIG. 3 is a flow diagram of an example overview of the iterative OCRT reconstruction technique in accordance with embodiments of the present disclosure;

FIG. 4A is an image of a 1200-averaged OCT B-scan;

FIG. 4B is an image showing the histogram-matched OCRT reconstruction;

FIG. 4C are bar plots of the 2D Gaussian width (FWHM) fits (median, with 90% data coverage intervals after filtering out poor fits;

FIG. 4D shows the OCRT RI map for a polystyrene bead sample embedded in a 2% agarose gel reconstructed in FIG. 4B, and another OCRT RI map is shown for a separate polystyrene bead sample embedded in PDMS;

FIG. 5 is a perspective view of a rotation stage mount for multi-angle data collection of a microcapillary tube sample by OCRT in accordance with embodiments of the present disclosure;

FIG. 6 shows panels of images comparing the OCRT reconstruction and RI map to a conventional OCT B-scan and histological section of mouse vas deferens and femoral artery;

FIGS. 7A and 7B show panels of images comparing the OCRT reconstruction and RI map to a conventional OCT B-scan and histological section of mouse bladder and trachea;

FIG. 8 show panels of images comparing the OCRT reconstruction and RI map to a conventional OCT B-scan and histological section of human cornea and crane fly leg reveals additional RI information;

FIG. 9 shows graphs of horizontal and vertical cross-sections of the RI maps of the cornea samples in FIG. 8 and FIG. 10;

FIG. 10 compares the OCRT reconstruction and RI map to a conventional OCT B-scan and histological section of another human cornea sample;

FIG. 11 is a plot showing interpolating coordinate points after ray propagation;

FIG. 12 is a graph showing angular dependence of back-scattering intensity for biological samples inferred by OCRT;

FIG. 13 are images showing progression of OCRT optimization over several iterations; and FIG. 14 shows graphs that are additional OCRT results for relaxed mouse bladder wall.

SUMMARY

The presently disclosed subject matter provides systems and methods for imaging based on multiple cross-sectional images acquired at different angles. According to an aspect, a method includes acquiring multiple cross-sectional images of an object at different angles. The method also includes registering the acquired cross-sectional images. Further, the method includes reconstructing an enhanced resolution image of the object based on the registered images. The method also includes displaying an image of the object based on the enhanced resolution image.

According to another aspect, an OCRT system includes a conventional imaging system, to generate 2D or 3D cross-sectional images of a sample. The system also includes a mechanism acquire these images at angles up to 360 degrees. Furthermore, the system includes an algorithm that registers the 2D/3D images, reconstructs a higher resolution 2D or 3D image of the sample, and generates a 2D or 3D RI map of the sample. Further, the system includes a computing device that implements the aforementioned algorithm and displays the result.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. A computing device may be, for example, retail equipment such as POS equipment. In another example, a computing device may be a server or other computer located within a retail environment and communicatively connected to other computing devices (e.g., POS equipment or computers) for managing accounting, purchase transactions, and other processes within the retail environment. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD), or a smart watch or some other wearable smart device. Some of the computer sensing may be part of the fabric of the clothes the user is wearing. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g. Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although many of the examples provided herein are implemented on smart phones, the examples may similarly be implemented on any suitable computing device, such as a computer.

As referred to herein, the term "user interface" is generally a system by which users interact with a computing device. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface.

Embodiments of systems and method disclosed herein are referred to "optical coherence refraction tomography" or "OCRT," which can use multiple OCT cross-sectional images ("B-scans"), which can be 2D or 3D, acquired at a diversity of angles (in 2D or 3D) to reconstruct isotropic, high-resolution, cross-sectional images with the superior axial coherence gating of conventional OCT extended to the lateral dimension. Alternatively, if the OCT system has a higher lateral resolution than axial resolution (such as in spectroscopic OCT (SOCT)), the superior lateral resolution may be used to improve the axial resolution up to the lateral resolution. Taken to the other extreme, if the OCT system is completely defocused or unfocused such that there is effectively no lateral resolution, OCRT still theoretically increases the lateral resolution up to the axial resolution limit. Here, "OCT" and "conventional OCT" are to be interpreted broadly to include all of its variants, such as, but not limited to, time-domain OCT (TD-OCT), spectral-domain OCT (SD-OCT), swept-source OCT (SS-OCT), full-field OCT (FF-OCT), line-field OCT (LF-OCT), optical coherence microscopy (OCM), spectroscopic OCT (SOCT), pump-probe OCT (PP-OCT), microscope-integrated OCT (MI-OCT), and stimulated Raman scattering OCT(SRS-OCT), all of which can have the shortcomings of anisotropic spatial resolution and refraction-induced spatial distortions. More generally, instead of OCT one may also use any imaging system with anisotropic spatial resolution, such as ultrasonic imaging, photoacoustic imaging, and their variants. Even more generally, instead of OCT, we may also use any imaging modality that suffers from sample-induced image distortions. However, herein the term "OCT" or "conventional OCT" is used. OCRT systems and methods disclosed herein can be used to address these shortcomings of conventional OCT. In the absence of refraction, light rays travel in straight lines and the reconstruction procedure is analogous to that of X-ray computed tomography (CT). However, due to refraction and optical path delays in the sample, OCT images acquired at multiple angles are distorted differently and hence need to be dewarped and registered. Thus, in correcting for sample-induced refraction, OCRT is unique for estimating the spatially resolved RI distribution of the sample, which is aligned with the high-resolution reconstruction. Other multiangle RI tomography techniques accounted only for path delay (not changes in ray direction), required access to the other side of the sample, and were not applied to biological samples. Focal shift-based OCT methods for depth-resolved RI measurement typically require experimental repositioning of the focus and physical depth scanning in the sample or reference arm. However, OCRT can be implemented using, for example, a suitable OCT system by rotating the sample or by use of a beam scanning protocol or a combination thereof in accordance with embodiments disclosed herein. The multiangle measurements need not be acquired sequentially, but can be acquired in a multiplexed fashion, such as by having multiple OCT systems viewing the sample at different angles, or by having a modified OCT system that simultaneously collections multiple angular views. Such strategies may be combined with sample rotation, beam scanning, or both.

FIG. 1 illustrates a block diagram of an example system for implementing optical coherence refraction tomography (OCRT) in accordance with embodiments of the present disclosure. Referring to FIG. 1, the system includes an image processor 100 configured to implement OCRT image processing. The image processor 100 may include memory 102 and one or more processors 104 for implementing the functionality described herein. Alternatively, the image processor 100 may include any suitable hardware, software, firmware, or combinations thereof for implementing the functionality described herein. The image processor 100 may be, for example, a computing device such as a desktop computer or laptop computer.

The system 100 may include an OCT scanning device 106 configured to scan an object 108, such as biological tissue, and to output image data representative of the scanned object 108. The image processor 100 may receive the output image data and store the data in memory 102. A user interface 110 (e.g., a keyboard and/or mouse) may be used by an operator (e.g., ophthalmologist, radiologist, etc.) to enter input. The image processor 100 may process the image data in accordance with embodiments disclosed herein. The processed data may be stored in memory 102 and may be displayed as an image and/or text on a display 112 of the user interface 110.

As OCRT can be described as a Fourier synthesis technique from multiangle illumination, it is useful to compare it to CT. A single 1D projection in CT can be considered an image resulting from the convolution of the 2D scene with a point-spread function (PSF) that is infinitely wide in projection dimension (x) and narrow in z. For example, FIG. 2A are images showing CT and OCRT (top row of images and bottom row of images, respectively) as both having anisotropic lateral and vertical point-spread functions (PSFs) and transfer functions (TFs). Referring to FIG. 2A, by adding contributions from multiple angles, frequency space is filled in and a TF is synthesized with larger frequency support (third and fourth columns). In the fourth column, a filter is applied prior to summation to attenuate low frequency components. Both techniques have the same theoretical synthesized PSF, assuming the same vertical spatial frequency bandwidth and sufficient angular coverage. Note that because OCT also could have lateral frequency support, coarser angular spacing is sufficient for OCRT, but not for CT (it is evident from the fourth column that more angles are needed to obtain the same result as in OCRT). It can be seen that, in Fourier space, the product of the 2D Fourier transform of the 2D scene and the kernel transfer function is a delta function in the x direction, and of finite width in the z direction (Fourier slice theorem). Hence, by taking projections at multiple directions, the entire 2D Fourier spectrum of the object can be synthesized up to the frequency cutoff defined by the resolution of the 1D detector and the diffraction limit. The inverse 2D Fourier transform then reconstructs the image with isotropic high-resolution. In practice, the backprojection algorithm can be employed, in which each 1D projection is uniformly smeared in the direction of the X-rays, and summed across all angles, which is mathematically equivalent to the Fourier synthesis technique in a continuous framework. Filtered backprojection (FBP) applies a filter to the 1D projections to account for the fact that the center is overrepresented, the ideal filter being the ramp filter, $H(f)=|f|$, which arises from the Jacobian of the transformation between Cartesian and polar coordinates. Other example filters, but are not limited to, Hamming, Shepp-Logan, cosine, Hann, or other suitable filters.

In some embodiments, OCRT and CT may be considered conceptually similar (See e.g., FIG. 2A), except that in OCRT the PSF in the projection dimension (x), defined by the lateral resolution, is not infinite but still wider than the PSF in the propagation dimension (z). Note that the projection dimension here is not necessarily the propagation dimension, but rather in general it is the dimension of the lowest resolution (in this case, the lateral dimension). Thus, if it is assumed that the lateral resolution is approximately constant with depth and that the wavefront curvature away from the focus of the Gaussian beam is negligible, the image is the convolution between the scene and an anisotropic PSF. In Fourier space, the transfer function corresponding to the PSF is anisotropic, with high frequency information diminished in one dimension. Analogously to CT, by taking B-scans at multiple angles, the missing high frequency information can be filled in. However, since OCT already has some lateral frequency support, OCRT requires data from fewer angles than CT. The angular spacing (assumed equal) depends upon the axial-to-lateral resolution ratio and the amount of tolerance on the gaps in the Fourier space at intermediate angles. As full angular coverage at ±90° is approached, isotropic resolution in the image plane, xz, is achieved (See e.g., FIG. 2D).

FIGS. 2B and 2C are diagrams and a graph, respectively, that show that angular spacings are dependent upon the axial-to-lateral resolution ratio and the amount of tolerance on the gaps in the Fourier space at intermediate angles. Referring to FIG. 2B, the finer the spacing of the angular data becomes, the smaller the gaps in the TF become. Circles 200 correspond to the radius of complete radial Fourier support, while circles 202 correspond to the nominal Fourier support. The minimum support, denoted as the ratio of the red radius to black radius, approaches 1 as the angular spacing decreases. The assumed OCRT axial-lateral PSF ratio for all four spacings is 0.30.

Now referring to FIG. 2C, the worse the lateral resolution is relative to the axial resolution, the finer the angular spacing required is. However, the larger the gaps acceptable in the TF, the larger the angular spacing can be. Point 204 corresponds to the settings used in the experiments (spacing=6°, axial-lateral ratio ~0.3, minimum Fourier support ~0.986).

FIG. 2D is a graph showing the axial-lateral ratio versus illumination angle $\theta_{max}$i. Referring to FIG. 2D, assuming sufficiently fine angular spacing, lateral resolution improves when the largest illumination angle $\theta_{max}$ increases and approaches the axial resolution as $\theta_{max}$ approaches full coverage)(±90°. Note that the previous Fourier description of OCRT and the accompanying FIG. 2 are in a 2D framework, but the same may be extended to 3D with two dimensions of angular scanning.

While RIs of biological tissue in the X-ray regime are close to 1, in the optical regime a spatially varying RI distribution distorts OCT images by changing the path lengths and the directions of the rays, preventing rigid-body registration among the multiangle B-scans. If the RI distribution are known, the rays may be propagated accordingly to dewarp the image prior to FBP application to generate a high-resolution reconstruction. To infer the unknown RI distribution, in OCRT the inverse problem may be solved using, for example, the ray equation as the forward model, which in 2D (x and z) is $$\frac{d}{ds}\left(n_A \frac{dx}{ds}\right) = \frac{\partial n_A}{\partial x}, \frac{d}{ds}\left(n_A \frac{dz}{ds}\right) = \frac{\partial n_A}{\partial z}, \quad (1)$$

where $n_A(x,z)$ is the RI distribution parameterized by A and s is the position along the 1D ray trajectory. The parameterization can be a sum of a regularly spaced grid of Gaussian kernels such that $n_A(x,z)$ is differentiable everywhere and minimizes the effects of the "staircase" artifacts stemming from discretization onto a Cartesian grid. In particular, an index distribution given by the Nadaraya-Watson kernel parameterization is one example choice, which avoids having to use finite differences to compute spatial gradients, as analytic expressions are available. Other suitable parameterizations of the RI distribution may be used. Additionally, other methods for solution of the forward ray propagation problem (such as other analytical or computational approaches which are known in optics) may be used. Furthermore, in addition to methods for ray propagation, methods for wave propagation and photon diffusion may be used.

Because in general there is no closed solution to the ray equation, numerical integration (fourth-order Runge-Kutta) was employed. To specify optical path delay, a constant step size may be used for the numerical solver, which can be scaled by the inverse of the RI value at the current position of the ray. To initiate ray propagation, the initial conditions are to be specified, which correspond to the initial ray positions and directions. For example, assuming telecentric scanning and uniform sampling of A-scans within each B-scan, the initial directions are all parallel, and the initial positions are equally spaced for each angle. In this way, the A-scans can be propagated from each B-scan from each angle as individual rays, which cause the overall B-scan image to dewarp. In theory, if the optimal RI distribution is found, the images would be perfectly registered. It can be assumed that the group and phase indices are approximately the same in biological tissue (minimal chromatic dispersion), such that a common index distribution governs both path trajectory and delay. Thus, herein the terms group (refractive) index and RI are used interchangeably. However, it is possible for OCRT to reconstruct the group and phase refractive indices separately by treating them as separate parameters in the optimization algorithm.

To provide feedback on the accuracy of $n_A(x,z)$ to aid its optimization, a differentiable metric may be used that quantifies the degree of joint registration among all the B-scans. Here, an intensity-based metric is described, by which the mean squared error (MSE) between the raw B-scans and a forward prediction of the B-scans may be computed based on the estimated high-resolution reconstruction. However, other metrics may be used, such as those used by point-set-based registration techniques. However, other metrics may also be used. For example, FIG. 3 illustrates a flow diagram of an example overview of the iterative OCRT reconstruction technique in accordance with embodiments of the present disclosure. Referring to FIG. 3, multiangle B-scans served as the input, which are backprojected along trajectories derived from ray propagation (ray prop) according to the current estimate of the RI distribution to form an estimate of the high-resolution reconstruction. The same trajectories sample the current high-resolution estimate to generate forward predictions of the B-scans. The mean square error (MSE) between the B-scan data and B-scan estimates may be iteratively minimized with respect to the RI distribution. The forward model may start with the current estimate of the high-resolution reconstruction based on FBP along the ray trajectories governed by the current estimate of the RI distribution. For each B-scan orientation, that current estimate may subsequently be rotated, warped according to the same trajectories, blurred by the OCT PSF, depth-wise attenuated, and locally intensity-rescaled according to the orientation of the structure to the illumination. The result constitutes the forward prediction of the B-scan, the MSE between which and the raw B-scan data is to be minimized with respect to the forward model parameters (e.g., the RI distribution, attenuation parameters, etc.). Further, regularization on the index distribution may be implemented to impose spatial smoothness, stabilizing the solution and optimization. After registration, the filter for FBP may be optimized. The filter may also be jointly optimized as a forward model parameter alongside the RI distribution, attenuation parameters, etc. Alternatively, instead of using FBP to generate the high-resolution reconstruction, the high-resolution reconstruction may itself be a parameter that is optimized jointly with the forward model parameters (e.g., the RI distribution). Furthermore, regularization terms may be added that relate the RI map and OCRT reconstruction, since in theory OCT image contrast derives from the RI. Although an intensity-based metric is described here, other metrics may be used such as, but not limited to, point-set-based metrics or any other suitable metrics that quantify the degree of registration among the multiangle images.

A modified version of gradient descent called Adam may be used to minimize this regularized MSE, which jointly registered the B-scans and estimated both the RI distribution and the high-resolution, isotropic image. Other gradient-based optimization methods may be used such as stochastic gradient descent, Adagrad, Adadelta, and Nesterov momentum, among many others. The gradient of the intensity-based registration metric may be computed through the numerical differential equation solver with respect to forward model parameters using TENSORFLOW™, a software library that employs automatic differentiation, a widely used technique in the deep learning community requiring only the specification of the differentiable forward model from which the gradient is computed through recursive application of the chain rule. Other deep learning software may be used, such as PYTORCH, CHAINER, DYNET, among many others. More generally, any framework that can implement gradient-based optimization may be used. Although gradient-based optimization is described here, gradient-free optimization algorithms such as evolutionary algorithms and other stochastic optimization methods may be used. In summary, the OCRT optimization procedure simultaneously registers all B-scans, generates an undistorted, isotropic, high-resolution reconstruction, and a co-aligned estimate of the RI distribution of the sample.

To validate the isotropic resolution of OCRT, 560-nm polystyrene beads embedded in a 2% (w/v) agarose gel inside a glass microcapillary tube were imaged, as shown in FIG. 4A, which illustrates an image of a 1200-averaged OCT B-scan. A custom-designed inverted rotation stage (See e.g., FIG. 5) was used to rotate the tube sample, which was immersed in water to reduce the RI contrast with the glass tube wall. FIG. 5 illustrates a perspective view of a rotation stage mount for multi-angle data collection of a microcapillary tube sample. This rotation stage mount was placed atop an xyz translation stage. Because the index contrast was still large, the applied optimization procedure started with gross estimation of the index distribution by first assuming a circular tube geometry and optimizing with respect to only the index of the medium and the glass, with the tube diameter, wall thickness, and center calibrated in a separate step. The subsequent optimization step refined this gross estimate by allowing the entire 2D index distribution to vary arbitrarily, as well as small translations of the OCT B-scans. Cylindrical tubes were used in this first proof of concept experiment to aid in sample mounting and rotation.

To quantify the resolution of OCRT, the beads of both the reconstruction and the averaged volume were localized. Also, a 2D Gaussian function with axes oriented with the Cartesian coordinate system was fit, where z and x are the axial and in-plane lateral dimensions, respectively (for the reconstruction, the x and z axes are arbitrary). The resulting distributions of the PSF width fits in x and z (See FIG. 3A) demonstrate a factor of greater than 3 enhancement in the lateral resolution and confirm that the resolution afforded by OCRT is isotropic, given by the axial resolution of the original OCT images.

FIG. 4B is an image showing the histogram-matched OCRT reconstruction. The two sets of close-up views (boxes 400, 402, 404, and 406; dashed outline (boxes 400 and 404) in averaged B-scan and solid outline (boxes 402 and 406) in OCRT reconstruction) show clear lateral resolution enhancement. Arrows in the zoomed-in views indicate beads resolved in the OCRT reconstruction, but not in the averaged B-scan. The arrows in the 2 zoomed-in views on the right in particular show beads in very close proximity, not resolved in the B-scan but visible in the OCRT reconstruction.

FIG. 4C are bar plots of the 2D Gaussian width (FWHM) fits (median, with 90% data coverage intervals after filtering out poor fits; numerical labels are the medians) demonstrate a >3-fold enhancement in lateral resolution, and that the spatial resolution of OCRT is isotropic. Note that for OCRT, the x and z axes were defined arbitrarily. The left column of FIG. 4D shows the OCRT RI map for the polystyrene bead sample embedded in a 2% agarose gel reconstructed in FIG. 4B. The right column of FIG. 4D shows the RI map for a separate polystyrene bead phantom, which was instead embedded in PDMS, which has a higher index. The estimated RI values for the embedding media fall within the uncertainty range (dotted lines represent one standard deviation) of the values estimated using OCT (see methods section). Scale bars are 100 µm.

To validate the RI distribution estimates, another bead phantom was made substituting the agarose gel for polydimethylsiloxane (PDMS). FIG. 4D shows that the OCRT index estimate was in good agreement for both agarose and PDMS, falling within one standard deviation of the bulk RI estimated independently from OCT pathlength measurements.

To demonstrate the performance of our method, OCRT was imaged and applied to a variety of ex vivo biological samples, including several mouse organs (vas deferens, femoral artery, bladder, and trachea), a human donor cornea, and a marsh crane fly (*Tipula oleracea*) leg. All samples were inserted into microcapillary tubes for convenience during imaging, and hematoxylin and eosin (H&E)-stained histological sections of neighboring tissue samples were obtained for comparison (also Masson's trichrome stain was obtained for the artery sample). Overall, it was observed that lateral resolution was significantly improved in the OCRT reconstruction across all samples imaged, and that the features in the RI maps matched features in the OCRT reconstructions. FIG. 6 shows panels of images of an example OCRT of mouse vas deferens and femoral artery. Panel "a" of FIG. 6 shows 1200-averaged B-scan of mouse vas deferens, histogram-matched to panel "b" of FIG. 6, the corresponding OCRT reconstruction. Panel "c" of FIG. 6 shows RI map that registers the multiangle B-scans. Panel "d" of FIG. 6 shows a histology from the vas deferens of a separate animal. Panels "e," "f," "g," and "h" show zoomed-in views of regions of interest in panel "a" and "b". Panels "i"-"p" show the same images from another vas deferens sample from a different animal. In both samples, it can be seen that structures in the adventitia (Ad) are better resolved in the OCRT reconstruction, in particular where the adventitia is artifactually detached (see panel "d"). The adventitia manifests as a darker shade and of a different texture than the smooth muscle layer (SM) in panel "b," consistent with the histology in panel "d". The transitional epithelia (TE), lumina, and lamina propria (LP) are more apparent in the OCRT reconstruction, while in the B-scan depth attenuation makes interpretation difficult. Panels "q"-"x" show the same images for a mouse femoral artery with a collapsed lumen. Panel "t" shows two adjacent histological slices of femoral artery from a separate animal—the top slice was stained with H&E and the bottom slice was stained with Masson's trichrome stain to accentuate the internal and external elastic lamina (IEL and EEL), which line the smooth muscle (SM). The internal and external lamina are clearly resolved in the OCRT reconstruction, consistent with the histology, while not apparent at all in the B-scan. It is noted that the undulatory structure of the internal lamina is very clear in the OCRT reconstruction, consistent with histology. Scale bars are 100 μm.

In the first vas deferens sample (panels "a"-"h" of FIG. 6), the structures of the adventitia, smooth muscle, lamina propria, and the transitional epithelium are clearly resolved. For example, it is apparent in the OCRT reconstruction but not in the B-scan (see panels "a" and "b" of FIG. 6) that the smooth muscle layer consists of more circumferential structure, in contrast to the adventitia, which has a different texture; this is consistent with the histology (see panel "d" of FIG. 6). Furthermore, the lamina propria is very prominent in the OCRT reconstruction as a darker, more strongly scattering layer, unlike in the histology where the delineation is subtler, and the clover-leaf-shaped transitional epithelium is much more recognizable in the OCRT reconstruction than in the B-scan. In the second vas deferens sample (see panels "i"-"p" of FIG. 6), in addition to the features in the first vas deferens sample, we observe clear evidence of resolution enhancement in the artifactual ribbon-like detachments of the adventitia, consistent with the histology (see panel "l" of FIG. 6).

In the mouse femoral artery sample (see panels "q"-"x" of FIG. 6), the smooth muscle layer and the external and internal elastic lamina are much more apparent in the OCRT reconstruction, while essentially invisible in the B-scan. Note in the OCRT reconstruction the undulatory pattern of the internal elastic lamina (see panels "v" and "x"), consistent with the Masson's trichrome-stained histology, which accentuates the elastic lamina as with a blue color (see panel "t" of FIG. 6, bottom slice). The internal elastic lamina is lined by nuclei in the OCRT reconstruction, appearing as dark dots (see panel "x" of FIG. 6), which is consistent with the H&E-stained histological slide (see panel "t" of FIG. 6, top slice).

FIGS. 7A and 7B show panels of images of an example OCRT of mouse bladder and trachea. Panel "a" of FIG. 7A shows a 1200-averaged B-scan (inverted) of a mouse bladder sample, histogram-matched to the image of panel "b," the corresponding high-resolution OCRT reconstruction, which shows the layers of the smooth muscle (SM) more clearly than in the B-scan. Furthermore, connective tissue structures in the lamina propria (LP) are much better resolved. Panel "c" of FIG. 7A shows an RI map that registers the multiangle B-scans, which exhibits two distinct layers, corresponding to the smooth muscle (SM) layer and the transitional epithelium (TE). Panel "d" of FIG. 7A shows an H&E-stained histological section from the same animal. Panels "e"-"h" show close-up views of regions of interest of the OCT B-scan and OCRT reconstruction denoted in panel "a" and "b". Panel "i"-"p" of FIG. 7B show the same images except for mouse trachea (B-scan also inverted). The histology in panel "l" was obtained from a separate animal. The basement membrane (BM) and ciliated epithelium (CE) are well resolved throughout the entire sample, while partially for the averaged B-scan. The cartilaginous (C) structures are also clearer in the OCRT reconstruction. The adventitia (Ad) is delineated by another dark line that is not readily apparent in the B-scan. Scale bars are 100 μm.

In the mouse bladder sample of panel "a"-"h" of FIGS. 7A and 7B, the layered structures of the smooth muscle are much clearer in the OCRT reconstruction than the B-scan, where they are less apparent due to lower lateral resolution and presence of speckle noise. The connective tissue in the lamina propria is also better resolved in the OCRT reconstruction. In particular, comparison of panel "e" and panels "g"-"f" and "h," respectively, reveals connective tissue features of the lamina propria present in the OCRT reconstruction, but not in the B-scan. In the mouse trachea sample (panels "i"-"p"), the basement membrane and ciliated epithelium are well resolved across the entire sample as dark lines, while only partially visible in the B-scan where they are near normal to the optical axis, suggesting that the anisotropic resolution of the B-scan is the culprit. The round cartilaginous structures are also clearer in the OCRT reconstruction.

FIG. 8 show panels of images of an example OCRT of human cornea and crane fly leg reveals additional RI information. Panel "a" shows a 1200-averaged B-scan of human cornea, histogram-matched to the image of panel "b," the corresponding high-resolution OCRT reconstruction. Panel "d" shows a histology from the same cornea sample. Panels "e"-"h" show zoomed-in views of regions of interest in panel "a" and "b". The lamellar structures of the stroma (St) are more clearly defined in the OCRT reconstruction and consistent with histology. The epithelium (Ep) and Descemet's membrane (DM) are also apparent, although partially damaged from processing (Ep damage is consistent with histology). The RI map in panel "c" is further analyzed in FIG. 9, and agrees with literature values, with RI values ~1.38-1.40. Panels "i"-"l" show information analogous to that of a-d for crane fly femur (Fem) and tibia (Tib). The outer wall of the femur (cuticle; Cu) is apparent in the OCRT reconstruction, as can be seen in the histology (l). Small hair-like protrusions of the cuticle (setae; Se) can also be observed in the OCRT reconstruction. The circumferential orientation of the longitudinal muscle fibers (LMF) are clearer in the OCRT reconstruction than B-scan. The RI map (k) shows an index close to the image in panel "l" inside the tibia, while close to that of water inside the femur, which is not immediately apparent in the B-scan (l). Scale bars are 100 μm. The human donor cornea sample is shown in Panel "a"-"h" of FIG. 9. The lamellar structures of the corneal stroma are parallel to the front and back surfaces of the cornea. Thus, the features of the stroma are largely axial and hence the increase in resolution for OCRT over the B-scan is not immediately appreciable, but rather the visibility of the lamellae increases due to speckle reduction (see also FIG. 10). More interestingly, the refractive index maps generated by OCRT (FIG. 9) range from 1.38-1.40, which agrees with previous bulk group index measurements at similar near-infrared wavelengths, considering the influence of dehydration on the index. Similar results were obtained on a different human cornea sample (Supplementary sec. 3), giving additional validation to the RI-mapping capability of OCRT.

Finally, the OCRT reconstructions of the tibia and femur cross sections of a crane fly (j) exhibit superior resolution of the outer walls (cuticle) and the ultrafine features that surround them. The cuticle, apparent as a thin orange structure in the H&E, manifests at the bottom of femur as two thin dark lines in the OCRT reconstruction. It is noted that although the larger hair-like structures (setae) present in the B-scan and OCRT reconstruction are not visible in the H&E, likely lost during tissue processing, the much finer setae lining the wall in the H&E are still visible in the OCRT reconstruction. The circumferential orientation of the internal longitudinal muscle fiber is also much more apparent in the OCRT reconstruction than in the B-scan. Furthermore, the RI map indicates that the lumen of the tibia was filled with air (n≈1) while the lumen of the femur was filled with water. Although this is disparity is likely due to the sample preparation procedure, it is a feature not at first apparent from the B-scan. However, upon closer inspection, we note that the region indicated by the green arrow in FIG. 6i is displaced upward relative to the regions in the neighboring A-scans that do not include the tibia lumen, which indicates that the tibia lumen has a lower RI (i.e., air). Furthermore, it is noted that the tissue-to-lumen interface is more intense in the tibia than in the femur, indicating a larger index contrast. Thus, the RI mapping capabilities of OCRT can reveal additional information about the sample and simultaneously dewarp the image.

FIG. 9 shows graphs of horizontal (h) and vertical (v) cross-sections of the RI maps. Graphs "a" and "b" are horizontal and vertical cross-sections, respectively. Graphs "c" and "d" are the horizontal and vertical cross-sections. All cross-sections are through the center of the tube lumen.

FIG. 10 shows images of OCRT of an additional human cornea sample. The subpanel organization is the same as that in FIGS. 6-8, except without histology in this case. The B-scan is inverted. Because the structures of the stroma are largely axial, the major improvement of the OCRT reconstruction over the B-scan is speckle reduction. The RI map in c is further analyzed in FIG. 9. Scale bars are 100 µm.

As disclosed herein, OCRT is provided and may use OCT B-scans from multiple angles to simultaneously reconstruct an undistorted, isotropic, high-resolution image and estimate the RI distribution. In particular, the superior axial resolution of OCT is extended to the inferior lateral resolution to form an isotropic PSF. Resolution enhancement and RI estimates of OCRT are demonstrated not only in sub-resolution scattering bead phantoms, but more importantly in several biological samples.

As an example, OCRT is advantageous over other techniques that address the depth-of-focus tradeoff because it can replace the lateral resolution dependence on diffraction with the axial resolution dependence on coherence. For example, recent work in applying OCT to the extreme ultraviolet regime has yielded axial resolutions on the order of 10s of nm, but with lateral resolutions three orders of magnitude lower. Since OCRT does not require high-NA objectives, much longer working distances associated with low NAs are possible, which make in vivo imaging more practical. Moreover, OCRT can tolerate lateral aberrations, in particular those induced by the sample. While the resolution of OCRT can be degraded by chromatic dispersion induced by the sample, in principle they can be corrected computationally. Another advantage of OCRT over other inverse optimization approaches is that it does not require phase stability, which for near infrared wavelengths typical of OCT requires nanometer scale stability of both the scanner and the sample over the acquisition time. On the other hand, OCRT, which employs intensity images, only requires stability on the order of the axial resolution, and even this constraint may in principle be relaxed through computational corrections during the registration step. Another advantage is the speckle reduction due to angular compounding of independent speckle patterns.

In accordance with embodiments, OCRT imaging systems and methods disclosed herein provide a general framework that leverages multiangle OCT images to computationally synthesize both an enhanced-resolution reconstruction and an RI map. Substantial improvements of OCRT over OCT in various biological samples are described, and it was found that there were structures readily apparent in OCRT reconstructions but missing in conventional OCT images.

OCT images shown in the figures were acquired using a commercial spectral domain OCT system (Bioptigen Envisu R4110)MR SDOIS) at a 20-kHz A-scan rate, with an incident power of 1 mW, an 820-nm center wavelength, and a nominal axial resolution of 1.2 µm in air and lateral resolution of 8.5 µm. The B-scans consisted of 500 A-scans over a field of view of 1.5 mm; each A-scan had 2048 pixels with a maximum imaging depth of 2.22 mm in air. This is just one example of an imaging system that acquires distorted, lower resolution images at multiple angles; however, as mentioned earlier, other imaging systems may be used (e.g., other variants of OCT, ultrasound imaging, photoacoustic imaging, etc.).

In one use case, for each sample, 20-averaged OCT B-scans or volumes every 6° across 360° were acquired. For the polystyrene bead phantoms only, out-of-plane averaging of B-scans was performed across 18 frames spaced 3 µm apart to account for slight tube misalignment, due to which the beads close to the wall of the tube away from the axis of rotation, because of their small size, were not present in every B-scan. These y-averaged B-scans were used as the raw data for OCRT reconstruction. For all biological samples this was not an issue and so the B-scans were not averaged across the y direction.

All samples were inserted into capillary microtubes (provided by Drummond Scientific Microcaps) with an inner diameter of 797.6 µm and immersed in phosphate buffered saline (PBS). 560-nm polystyrene beads (provided by Thermo Scientific) were embedded in 2% agarose gel (provided by Sigma Aldrich) or PDMS (provided by Dow Corning). Tube insertion is an example technique to facilitate multiangle image acquisition, in this case through sample rotation.

The animal organs used in this study were from mice (C57BL/6 wild-type). The organs were fixed in 10% neutral buffered formalin (NBF) and kept at 4° C. for 24 hours. After fixation, all organs were micro-dissected using an upright Zeiss dissection scope. The dissected tissues were inserted into the glass microtubes using dissection forceps. In some instances, the tissues were placed into the glass tube following aspiration with a 23G truncated needle on the opposite side of the tube. This procedure allowed the specimen to gently slide into the inner wall of the glass microtubule. To avoid dehydration after fixation, all specimens were transferred with the glass tube in PBS. The remaining organ tissue was used for paraffin block preparation followed by H&E staining or trichrome staining for histological examination. Histological images were acquired at 10× or 20× magnification using an Olympus microscope and digitally white balanced.

N=8 tubes were sampled and their inner diameters estimated using OCT by measuring the difference between the luminal reflections, and obtained 797.3±0.9 µm (standard error of the mean), in very good agreement with the manufacturer's specification of 797.6 µm. The inner diameter pathlength of the bead samples (with either agarose or PDMS embedding media) were estimated using the same method for all angles and volume (y) slices, across which the standard deviation values in FIG. 3d were calculated.

To acquire images at multiple angles, a custom-built, inverted rotation stage (Thorlabs) was designed and made to mount a single tube vertically. The tube had two orientation degrees of freedom and two translational degrees of freedom perpendicular to the axis of rotation, which we use to manually align the tube. The tube was immersed in water or PBS in a cuvette, which remained stationary during sample rotation. The entire above setup was mounted on xyz-translation stage as shown in FIG. 5. Sample rotation and data acquisition were automated using a custom Python script. For all experiments, we acquired B-scans at 60 orientations, spaced evenly across 360°.

Optimization was conducted on TensorFlow 1.8 using Python 2.7 on an Intel Core i7-3930K with 48 GB of RAM. Because each iteration required 10s of GB of memory, the CPU version of TensorFlow was used. For all samples we ran gradient descent for 200-500 iterations, on the order of a 2-3 minutes per iteration. Filter optimization was run for an additional 100 iterations. The same hyperparameters were used for all biological samples.

Here, an example image dewarping model based on the ray equation is provided, although other suitable image deformation models may be used. A 2D ray equation is given by Equation 1, but because s is the position along the 1D ray trajectory, we may use one of the two equations, and use the relationship $$ds = dz\sqrt{1 + \left(\frac{dx}{dz}\right)^2}.$$

Thus, we used a single nonlinear, second-order differential equation:

$$\frac{d^2x}{dz^2} = \frac{1}{n_A}\left(\frac{\partial n_A}{\partial x}\left(1 + \left(\frac{dx}{dz}\right)^2\right) - \frac{\partial n_A}{\partial z}\frac{dx}{dz}\right) \quad (2)$$

As discussed herein, because there is in general no closed solution to the ray equation, a fourth-order Runge-Kutta (RK4) numerical integration was used on Equation 2 to obtain the ray trajectory, x(z). To specify changes in optical path length, the RK4 step size can be divided by the RI at the current position. In principle, a ray may be propagated for each A-scan, but in practice an approximation may be used and propagated as a smaller number of rays. Because the RK4 solver is an iterative chain of element wise tensor multiplication operations, it is differentiable.

Equation 2 requires the spatial gradient of $n_A$ at any arbitrary position (x,z). Furthermore, because gradient descent may be used for optimization. Second-order, mixed partial derivatives of $n_A$ may be available (i.e., $$\frac{\partial^2 n_A}{\partial x \partial a} \text{ and } \frac{\partial^2 n_A}{\partial z \partial a}$$

for all $\alpha \in A$). One such parameterization is the Nadaraya-Watson parameterization using the Gaussian kernel, given by $$n_A(x,z) = \frac{\Sigma_{i,j} A_{i,j} \exp\left(-\frac{(x-x_i)^2 - (z-z_j)^2}{2\sigma^2}\right)}{\Sigma_{i,j} \exp\left(-\frac{(x-x_i)^2 - (z-z_j)^2}{2\sigma^2}\right)}, \quad (3)$$

which is a weighted sum of Gaussian kernels of uniform width σ and heights given by matrix A, which in our experiments had dimensions 128 by 128 covering a field of view of ~1.6 by 1.6 mm. The kernel positions may be given by $x_i$, $z_i$, which were regularly spaced on a 2D grid in experiments. An analytical expression for the gradient of Equation 3 at an arbitrary position is also available. This parameterization may be chosen because sharp index boundaries were approximated as smooth transitions, especially if the RK4 step size is larger than the resolution of the index distribution. It was found that propagating rays at a boundary between two uniform media with this approximation agreed with Snell's law. Another reason was that we encountered "staircase" discretization artifacts, whereby an interface oblique to the coordinate axes would be locally parallel or perpendicular if some form of higher order interpolation is not used.

To ease the computational burden, several approximations may be made. For example, it was found that setting the RK4 step size to be the axial length of one pixel (in air) of an A-scan was too computationally demanding. Instead, the following may be made: let the step size cover p=8 pixels (~8 μm) and use linear interpolation made to fill in the intermediate positions within the step. Likewise, it was found that propagating one ray per A-scan (~380) was also too computationally demanding, so the rays may be downsampled to a fixed k=35 rays. The coordinates of the intermediate rays may be spaced evenly between neighboring propagated coordinates.

Since Equation 3 in practice may be too computationally demanding, when the index and index gradient at $(x_i, z_1)$ are sought, only a neighborhood of 7 by 7 kernels may contribute to the weighted sum (rather than every single kernel). As mentioned, it is noted that the first two approximations may affect the spatial resolution of the RI map.

To aid in optimization of the RI distribution, before A is allowed to vary arbitrarily, optimization with respect to parameters describing the tube geometry may be implemented. For example, there may be six parameters: the inner and outer radius of the tube, the medium index, the tube wall index, and the xz coordinates of the center of the tube. The inner and outer radii may be independently calibrated using OCT, and estimated the center of the tube in a separate optimization. Thus, only two RI values could be optimized. This may allow for a better initial guess for A. This procedure may be applied for a calibration sample, such as the polystyrene bead sample embedded in agarose gel, and values similar used to the resulting parameters may be used to seed the optimization for all biological samples.

The A-scans are backprojected along those trajectories according to the RI map rather than along straight lines as part of the image registration. Because fewer rays (k=35) than A-scans (~380) might be propagated and each RK4 step size may cover p=8 axial pixels (Sec. 1.3), for all the other points the two closest rays may be identified to be propagated (one to the left, one to the right of the points) and on those rays the two closest depths (one above, one below) that were multiples of p (i.e., a depths at which the RK4 solver stepped). These four corner points describe the smallest rectangle (whose vertices were propagated points) that surrounded the points, which were evenly spaced with respect to these four points using a bilinear interpolation scheme (see FIG. 11). In this way, every pixel in the B-scans had an interpolated coordinate. Other interpolation schemes may be used, and may be extended to 3D.

FIG. 11 is a plot showing interpolating coordinate points after ray propagation. Referring to FIG. 11, the four large black corner points correspond to two consecutive steps of the RK4 solver on two neighboring rays. All the smaller circles (original) correspond to the centers of the pixels of the B-scan. After ray propagation, the four large (original) corner points were transformed to the large corner (transformed) points. The smaller points denoted by the small circles were transformed according to a bilinear interpolation scheme.

To do the backprojection, a tensor R of dimensions $n_{x2} \times n_{xz} \times n_y$ may be defined, choosing $n_{xz}$ such that the pixel size may be chosen appropriately to match the expected resolution of the reconstruction. In experiments, a single averaged B-scan was obtained from each angular view, so $n_y$ was set to 1. The values corresponding to the individual spatial coordinates for the B-scan pixel positions (which have been rotated, warped, and interpolated based on the propagated rays) may be distributed to fixed neighborhoods of pixels, weighted by the Gaussian kernel distance of each pixel to the spatial coordinate being projected. Other interpolation schemes may be used to reduce pixel-level artifacts.

Because the rays are no longer necessarily parallel after image dewarping, some parts of the final image could have more dense contribution (e.g., due to ray focusing); to account for this, normalization may be implemented by element-wise division by the coverage of the backprojection, which can be computed by backprojecting tensors of is whose sizes match those of the B-scans. In this way, the values accumulated in pixels in the reconstruction via backprojection that were visited by rays more times would be divided by larger numbers. This normalization scheme may be applied first for each B-scan, and finally for the full reconstruction.

Since backprojecting the raw B-scans may result in strong emphasis on the low spatial frequencies (FIG. 1), FBP may be used by applying to each A-scan individually a filter that deemphasizes low frequencies, such as the Ram-Lak filter, $H(f) \propto |f|$, as is often done in CT. To counteract noise, instead the square root of the Ram-Lak filter was used, $H(f) \propto \sqrt{|f|}$, which attenuates the higher frequencies to some extent. Other filters may be used. After registration, the filters were optimized.

The intensity-based registration metric may be the mean squared error between the B-scan data and the B-scan prediction generated by the forward model from an iterative estimate of the high-resolution reconstruction.

Given the current estimate of the RI distribution, the rays may be propagated, and the B-scan pixel values were interpolated and backprojected as described herein. Let R denote the current estimate of the high-resolution reconstruction result. To generate B-scan predictions, the coordinates of the same propagated rays were used for backprojection to gather the reconstruction intensity values. In particular, for each coordinate along the rays, the intensities of a fixed neighborhood of pixels may be gathered and their mean computed, weighted by the Gaussian kernel distance to the pixels.

To make this B-scan prediction more accurate, optimizable parameters may be included that describe for example: 1) the angular dependence of backscattering, 2) the anisotropic point-spread function (PSF) of OCT, and 3) the axial attenuation (in this order).

OCT analyzes backscattered light whose intensity varies as a function of angle between the illumination and the orientation of the interface. Namely, if we image a flat surface, the backscattered intensity at normal incidence can be expected to be the highest and at near parallel incidence to be the lowest. Moreover, the angular dependence of the backscattered intensity depends strongly on the roughness of the surface (e.g., the backscatter intensity may be independent of angle for a sufficiently rough surface).

Since the angular dependence of any specific sample is unknown, it may be treated as an optimizable parameter by discretizing the angular range of −90° to +90° into for example d=30 levels, so there were d parameters to optimize, which may be used to rescale the B-scan intensity values pixel-wise. To estimate these d parameters, the reconstruction estimate R may be convolved with d Gabor filters oriented at those d angles and for each pixel in the resulting convolution the index corresponding to the angle with the largest Gabor response may be found, resulting in an image of local orientations (one of d indices). Next, the same ray trajectories may be used to gather (using rounded coordinates) the orientations, resulting in an image of the same size as the B-scan of orientation indices, each pixel of which was assigned a value according to the orientation index (one of d). Finally, the B-scan prediction may be multiplied by this image. Example optimized angular backscatter profiles for biological samples are given in FIG. 12.

FIG. 12 is a graph showing angular dependence of backscattering intensity for biological samples. It is noted that the human cornea samples exhibit the most anisotropic backscattering profile, which agrees with the fact that structures in the stroma are oriented perpendicularly to the surfaces of the cornea (see FIG. 10). Similarly, the layers of the smooth muscle in the bladder become more parallel when the bladder is distended, and hence has a more anisotropic backscattering profile than the relaxed bladder. It is noted that the profiles are approximately symmetrical as expected, even though enforce symmetry was not explicitly enforced.

After the B-scan prediction is modified according to local orientation, it is convolved with a 1D Gaussian kernel, such that blurring only occurs in the lateral dimension.

Finally, a model may be incorporated to account for A-scan attenuation due to backscatter, absorption, and system sensitivity falloff. Accounting for attenuation may be necessary to prevent the RI from changing excessively from trying to account for registering A-scans at depths where there was no longer any signal. There was no attempt to separate the contributions to the axial attenuation, but rather nonparametrically modeled the total attenuation; as such, the parameters optimized for this purpose were not readily interpretable, but other parameterizations may be used to isolate the relative contributions. The following are defined:

B, the final B-scan prediction incorporating the angular backscatter profile, the OCT PSF, and axial attenuation;
B', an intermediate B-scan prediction, incorporating only the angular backscatter profile and OCT PSF; and
$B_{psf}$, incorporating only the OCT PSF.

Then, by deriving from Beer-Lambert's law, one may use (indexing rows, starting with 0)

$$B[i, :] = \alpha B'[i, :] \exp\left(-\beta \sum_{j=0}^{i} B_{psf}[j, :]^\gamma\right), \quad (4)$$

where α, β, and γ are optimizable parameters. $B_{psf}$ is used in the exponential because light incident obliquely on a surface might result in lower backscatter, and thus the backscatter signal could underestimate the attenuation due, for example, to a specular reflection that missed the collection optics. The y exponent allows this attenuation model freedom to deviate from Beer-Lambert's law to account for other sources of attenuation (e.g., falloff). More generally, the exponential may be any parameterizable function of $B_{psf}$, such as a Taylor expansion.

The MSE is then computed for each B-scan across all angles, which was then minimized iteratively.

Individual xz spatial translations for each B-scan may be allowed, to account for residual B-scan misalignment not explainable by RI. However, it was found that the amount of freedom allowed for the translations may affect the estimated RI values; in particular, it is possible for the optimization to move the B-scans away from the center and stretch the B-scans to compensate. Thus, regularization may be imposed on these translations as described herein.

Masked versions of L2 regularization and total variation (TV) regularization may be used on A. Instead of letting every pixel contribute equally to the regularization terms, the contributions may be weighted using a mask. In general, the outer boundary can in principle be determined because the shape of the first boundary is not distorted by refraction. Hence, L2 regularization may be used to constrain the region outside of the object being imaged to be close to the index of the immersion medium (e.g., the group index of water at 820 nm is ~1.342). Similarly, the TV regularization may be restricted to the inside of the object (e.g., to preserve boundary between the immersion medium and the sample).

Two regularization terms may be introduced for the xz translations ($\delta x_\theta$, $\delta z_\theta$), which are individually defined with respect to the coordinate system of each B-scan. One is a simple sum of squares deviation:

$$\Sigma_\theta \delta x_\theta^2 + \delta z_\theta^2 \quad (5)$$

The other counteracts expansion away from the center by penalizing B-scans separated by 180° for having similar z shifts:

$$\Sigma_\theta (\delta z_\theta + \delta z_{\theta+180°})^2 \quad (6)$$

This term encourages the relative distance between the two opposing B-scans to be close to 0 and hence counteracts the reconstruction from expanding or shrinking.

Once all the differentiable terms contributing to the loss are defined, which is a scalar, TensorFlow may be used to compute the gradient of this loss with respect to all the aforementioned optimizable parameters. Subsequently, this loss may be iteratively minimized using the Adam optimizer. FIG. 13 shows the OCRT reconstructions and RI maps for intermediate optimization states for two regions of interest. As mentioned herein, any suitable optimization algorithm may be used.

FIG. 13 are images showing progression of OCRT optimization over several iterations. Panel "a" of FIG. 13 corresponds to panel "h" of FIG. 7A, while panel "b" of FIG. 13 corresponds to panel "f" FIG. 14. Panel "i" indicates the iteration number, where i=0 corresponds to the state before optimization. The first rows show the reconstructions for various iterations i (all on the same color scale), and the second rows show the RI map for various iterations (the tube RI values saturate the chosen color scale to emphasize the sample values). The white boxes show the regions to which the OCRT reconstructions correspond. The arrows indicate particular features that have improved by the 100th iteration.

The ray gathering step uses only a small neighborhood of pixels and thus if the B-scans are grossly misregistered the optimization may get stuck in local minima. To combat this, a multiresolution approach may be used. For example, decreasing $n_{xz}$ of R increases the spatial coverage of each pixel, effectively increasing the local search range. Thus, the process may start a small $n_{xz}$ reconstruction size and periodically increase it during optimization. A multiresolution approach was used for the human cornea samples, starting with $n_{xz}$ that was ⅛ of the final reconstruction size and switching to the final size halfway through optimization.

After the aforementioned parameters (RI map, spatial shifts, attenuation, etc.) are optimized, all parameters may be frozen that may alter the ray trajectories and iterative optimization may be performed of the backprojection filter using the same intensity-based metric. This allowed the reconstruction to be more consistent with the B-scans by reducing potential filter-induced artifacts. For example, it was found that using the Ram-Lak or the square root of the Ram-Lak filter introduced a halo due to low energy at low frequencies. Although in principle it is possible to optimize the filters jointly with the registration parameters, it was empirically found that using a filter that attenuates higher frequencies (e.g., square root of Ram-Lak) can promote registration (likely in a similar way that a multiresolution resolution approach benefits from starting with low resolutions).

FIG. 5 shows an example rotation mount in accordance with embodiments of the present disclosure. The alignment procedure was as follows. First, a 100 μm by 100 μm by 6 mm (x by z by y) volume was scanned, and the tilt knobs were adjusted until the bright central reflection was as parallel to the y axis as possible at 90° intervals. Next, the xz translation knobs were adjusted until the entire tube cross section stayed at the same place for a 360° rotation. Any residual error can be corrected computationally.

In cases where the axis of rotation of the sample do not perfectly correspond to the center of the sample, each B-scan may be spatially translated so that the initial boundaries were registered. Fortunately, the initial boundary, in this case the tube outer wall boundary, is often easy to segment because it was the first bright reflection in the images. Then, let Q be the collection of all points corresponding to the initial boundary from all B-scans, let ($x_0$, $z_0$) be the coordinates of the virtual center of rotation that we wish to optimize such that the initial boundaries become registered, and let L be the axial-lateral aspect ratio. Assuming the absolute distance specified for the axial dimension of A-scans is trusted, L may be allowed to rescale the x coordinates. Next, without making any assumptions about the shape of the initial boundary, the full 360° was divided into angular slices $\{\Delta \theta_j\}_{j=0,1,2,...}$, where $\Delta\theta_j$ denotes the $j^{th}$ angular slice. The idea is that if the initial boundaries from multiple B-scans are well registered, the distances of initial boundary points from all B-scans to the center that reside in $\Delta\theta_j$ should be very close to each other, and thus we used the variance of those distances as a metric:

$$L_{initial}(x_0,z_0,L) = \Sigma_j \text{ var } \{\|((x-x_c)L,z)-(x_0,z_0)\|^2 | (x,z) \in (\Delta\theta_j \cup Q)\}, \quad (7)$$

where $x_c$ is a constant whose only purpose is to aid the optimization procedure by decoupling L and $x_0$.

OCRT may require careful calibration of the xz aspect ratio of the B-scans, because the final reconstruction formed from rotated B-scans no longer has this distinction. It was found that the estimated absolute RI values were sensitive to this calibration, and that one effective way to calibrate the aspect ratio was to use the axial dimension of OCT to measure the diameter of the tube and then during registration of the circular initial boundary constrain the diameter of the tube to the measured diameter. That is, we can add an extra term to Equation 7, $$\lambda(\text{mean } \{|((x-x_c)L,z)-(x_0,z_0)|^2|(x,z)\in Q\}-r_{meas})^2, \quad (8)$$

where $r_{meas}$ is the measured radius of the tube and $\lambda$ is a coefficient tuning this term's importance. This method was particularly effective because the same "ruler" (i.e., A-scan depth) was used both to measure the diameter and to define the axial coordinates of the B-scans, such that even if the A-scan depth was off by a scale factor, it would cancel out. This of course depended on the tube being perfectly circular, which we found to be a reasonable assumption from the tube maintaining the same distorted shape in the B-scans upon rotation. For more general samples (i.e., not embedded in a tube), precise methods would be needed to calibrate this aspect ratio.

In addition to the human donor cornea sample presented in panels "a"-"h" of FIG. 8, cornea was imaged, OCRT applied (see FIG. 8), and the RI values verified (FIG. 9) are also consistent with literature values. Interestingly, there is a RI gradient in the vertical direction, which is consistent in both cornea samples.

FIG. 10 shows additional OCRT of a human cornea sample (in addition to panels "a"-"h" of FIG. 8). The subpanel organization is the same as that in FIGS. 6-8, except without histology in this case. The B-scan is inverted. Because the structures of the stroma are largely axial, the major improvement of the OCRT reconstruction over the B-scan is speckle reduction. The RI map in c is further analyzed in FIG. 9, and agrees with literature values. Scale bars are 100 µm.

In FIG. 9, the graphs show horizontal (h) and vertical (v) cross-sections of the RI maps in panel "c" of FIG. 8 and panel "c" of FIG. 10. Panels "a" and "b" of FIG. 9 are horizontal and vertical cross-sections, respectively, of panel "c" of FIG. 8; likewise, panel "c" and "d" of FIG. 9 are the horizontal and vertical cross-sections of panel "c" of FIG. 10. All cross-sections are through the center of the tube lumen.

FIG. 14 shows graphs that are additional OCRT of relaxed mouse bladder wall. The subpanel organization is the same as that in FIGS. 6-8. The B-scan, panel "a," is inverted. From the OCRT reconstruction (shown in panel "b") it can be seen the connective tissue in the lamina propria much more clearly than in the B-scan, which is consistent with the histology, panel "d" (from a separate animal). In addition, the layers of the smooth muscle are more apparent in the OCRT reconstruction. Scale bars are 100 µm.

In experiments, an additional mouse bladder sample were also imaged, which is in a relaxed state (the bladder sample in the main text was distended). Lateral resolution enhancement is clear in the OCRT reconstruction, which increased the visibility of the smooth muscle layers and lamina propria, consistent with the histology.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. An imaging method comprising:
   acquiring a plurality of cross-sectional images of an object at different angles;
   registering the acquired cross-sectional images;
   reconstructing an enhanced resolution image of the object based on the registered images, wherein reconstructing the enhanced resolution image comprises using an iterative optimization algorithm, and wherein the iterative optimization technique maximizes a metric with respect to distortion parameters; and
   displaying an image of the object based on the enhanced resolution image.

2. The imaging method of claim 1, wherein the cross-sectional images are one of optical coherence tomography (OCT) B-scans and OCT volumes.

3. The imaging method of claim 1, wherein acquiring the plurality of cross-sectional images comprises using a scanning device to scan the object.

4. The imaging method of claim 1, wherein acquiring the plurality of cross-sectional images comprises one of rotating an illumination beam with respect to the object, rotating the object, and rotating an illumination beam.

5. The imaging method of claim 4, wherein acquiring the plurality of cross-sectional images comprises using an optical coherence tomography (OCT) scanning device for acquiring the plurality of cross-sectional images, and
   wherein the OCT scanning device is rotated up to 360 degrees.

6. The imaging method of claim 5, wherein acquiring the plurality of OCT cross-sectional images comprises rotating the object with respect to the OCT scanning device during scanning.

7. The imaging method of claim 6, wherein the object is rotated up to 360 degrees.

8. An imaging method comprising:
   acquiring a plurality of cross-sectional images of an object at different angles;
   registering the acquired cross-sectional images;
   reconstructing an enhanced resolution image of the object based on the registered images, wherein reconstructing the enhanced resolution image comprises applying filtered backprojection to the acquired OCT cross-sectional images after registration, and wherein applying filtered backprojection comprises taking a Fourier transform of each of the cross-sectional images, multiplying a result of the Fourier transform by filter, taking an inverse Fourier transform of each image, and superimposing all of the images resulting from the inverse Fourier transform; and
   displaying an image of the object based on the enhanced resolution image.

9. The imaging method of claim 8, wherein the filter is optimizable after or together with the registration.

10. The imaging method of claim 1, wherein displaying the image comprises using a display to display the image of the object.

11. The imaging method of claim 1, further comprising generating a distortion map based on registration of the images.

12. The imaging method of claim 11, further comprising displaying the distortion map.

13. The imaging method of claim 1, wherein acquiring the cross-sectional images comprises acquiring the cross-sectional images from one of photoacoustic imaging, ultrasound imaging, or other cross-sectional imaging technique having sample-induced distortion.

14. The imaging method of claim 1, wherein the distortion map is a refractive index map.

15. The imaging method of claim 1, wherein the registering and the reconstructing are performed simultaneously.

16. The imaging method of claim 1, wherein acquiring the plurality of cross-sectional images comprises acquiring the cross-sectional images from multiple angles simultaneously.

17. A system comprising:
- a scanning device configured to acquire a plurality of cross-sectional images of an object at different angles; and
- an image processor configured to:
  - register the acquired cross-sectional images;
  - reconstruct an enhanced resolution image of the object based on the registered images, wherein reconstruction of the enhanced resolution image comprises use of an iterative optimization algorithm, and wherein the iterative optimization technique maximizes a metric with respect to distortion parameters; and
  - control a display to display an image of the object based on the enhanced resolution image.

* * * * *